US00RE43372E

(19) United States
(12) Reissued Patent
deLong et al.

(10) Patent Number: US RE43,372 E
(45) Date of Reissued Patent: May 8, 2012

(54) C16 UNSATURATED FP-SELECTIVE PROSTAGLANDINS ANALOGS

(75) Inventors: Mitchell Anthony deLong, Raleigh, NC (US); David Lindsey Soper, Mason, OH (US); John August Wos, Maineville, OH (US); Biswanath De, Oro Valley, AZ (US)

(73) Assignee: Duke University, Durham, NC (US)

(21) Appl. No.: 12/479,532

(22) Filed: Jun. 5, 2009

Related U.S. Patent Documents

Reissue of:
(64) Patent No.: 6,586,463
Issued: Jul. 1, 2003
Appl. No.: 09/946,021
Filed: Sep. 4, 2001

U.S. Applications:
(63) Continuation of application No. 11/174,420, filed on Jul. 1, 2005, now abandoned, which is a continuation of application No. PCT/US00/05301, filed on Feb. 29, 2000.

(60) Provisional application No. 60/122,924, filed on Mar. 5, 1999.

(51) Int. Cl.
*C07C 405/00* (2006.01)
*A61K 31/5575* (2006.01)

(52) U.S. Cl. ..... 514/443; 514/530; 514/569; 514/570; 546/335; 549/58; 560/56; 560/60; 562/446; 562/469; 562/470

(58) Field of Classification Search ..... None
See application file for complete search history.

(56) References Cited

U.S. PATENT DOCUMENTS

| | | | |
|---|---|---|---|
| 13,294 | A | 7/1855 | Reynolds |
| 37,913 | A | 3/1863 | Howe |
| 37,914 | A | 3/1863 | Hankinson |
| 146,439 | A | 1/1874 | Ellis |
| 3,382,247 | A | 5/1968 | Anthony |
| 3,435,053 | A | 3/1969 | Beal et al. |
| 3,524,867 | A | 8/1970 | Beal et al. |
| 3,598,858 | A | 8/1971 | Bergstrom et al. |
| 3,636,120 | A | 1/1972 | Pike |
| 3,644,363 | A | 2/1972 | Kim |
| 3,691,216 | A | 9/1972 | Bergstrom et al. |
| 3,706,789 | A | 12/1972 | Bergstrom et al. |
| 3,723,427 | A | 3/1973 | Susi |
| 3,776,938 | A | 12/1973 | Bergstrom et al. |
| 3,776,939 | A | 12/1973 | Bergstrom et al. |
| 3,798,275 | A | 3/1974 | Finch et al. |
| 3,839,409 | A | 10/1974 | Bergstrom et al. |
| 3,852,337 | A | 12/1974 | Bergstrom et al. |
| 3,882,241 | A | 5/1975 | Phariss |
| 3,882,245 | A | 5/1975 | DuChame |
| 3,896,156 | A | 7/1975 | Beal et al. |
| 3,928,588 | A | 12/1975 | Robert |
| 3,934,013 | A | 1/1976 | Poulsen |
| 3,966,792 | A | 6/1976 | Hayashi et al. |
| 3,974,213 | A | 8/1976 | Hess et al. |
| 3,984,424 | A | 10/1976 | Schaff |
| 3,984,455 | A | 10/1976 | Beal et al. |
| 4,004,020 | A | 1/1977 | Skuballa et al. |
| 4,011,262 | A | 3/1977 | Hess et al. |
| 4,018,812 | A | 4/1977 | Hayashi et al. |
| 4,024,179 | A | 5/1977 | Bindra et al. |
| 4,051,238 | A | 9/1977 | Sokolowski |
| 4,061,671 | A | 12/1977 | Beck et al. |
| 4,073,934 | A | 2/1978 | Skuballa et al. |

(Continued)

FOREIGN PATENT DOCUMENTS

| | | |
|---|---|---|
| AU | 766163 | 10/2003 |
| BE | 746615 | 7/1970 |
| CA | 1339132 | 7/1997 |
| CA | 2364948 | 9/2000 |
| DE | 1801750 | 7/1969 |
| DE | 1617477 | 1/1970 |
| DE | 2255731 | 5/1973 |
| DE | 2355731 | 5/1974 |
| DE | 2409460 | 8/1974 |
| DE | 2460990 | 12/1974 |

(Continued)

OTHER PUBLICATIONS

Abramovitz, M. et al., "Cloning and expression of a cDNA for the human prostanoid FP receptor," J. Biol. Chem. (1994) 269:2632-2636.

Abramovitz, M. et al., "The utilization of recombinant prostanoid receptors to determine the affinities and selectivities of prostaglandins and related analogs," Biochimica et Biophysica Acta (2000) 1483(2):285-293.

Adis, Adisinsight: ZD-6416, AstraZeneca (United Kingdom) Mar. 27, 2000, 1 page.

AGN-192024, Pharmaprojects, HB4 S1G (2006).

(Continued)

*Primary Examiner* — Daniel Sullivan
*Assistant Examiner* — Yevegeny Valenrod
(74) *Attorney, Agent, or Firm* — Michael Best & Friedrich LLP

(57) ABSTRACT

Compounds having the general structure:

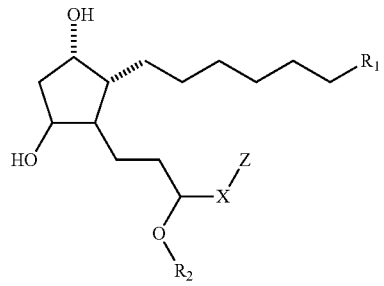

which are useful for the treatment of a variety of diseases and conditions, such as bone disorders.

66 Claims, No Drawings

U.S. PATENT DOCUMENTS

| | | | |
|---|---|---|---|
| 4,089,885 | A | 5/1978 | Husbands |
| 4,105,854 | A | 8/1978 | Gibson |
| 4,123,441 | A | 10/1978 | Johnson |
| 4,128,577 | A | 12/1978 | Nelson |
| 4,128,720 | A | 12/1978 | Hayashi et al. |
| 4,139,619 | A | 2/1979 | Chidsey, III |
| 4,152,527 | A | 5/1979 | Hess et al. |
| 4,154,950 | A | 5/1979 | Nelson |
| 4,158,667 | A | 6/1979 | Axen |
| 4,171,331 | A | 10/1979 | Biddlecom et al. |
| 4,206,151 | A | 6/1980 | Grudzinskas |
| 4,217,360 | A | 8/1980 | Vorbruggen et al. |
| 4,225,507 | A | 9/1980 | Sih |
| 4,225,508 | A | 9/1980 | Sih |
| 4,268,522 | A | 5/1981 | Eggler et al. |
| 4,284,646 | A | 8/1981 | Vorbruggen et al. |
| 4,296,504 | A | 10/1981 | Lawson |
| 4,311,707 | A | 1/1982 | Birnbaum et al. |
| 4,489,092 | A | 12/1984 | Vorbruggen et al. |
| 4,499,293 | A | 2/1985 | Johnson et al. |
| 4,543,353 | A | 9/1985 | Faustini et al. |
| 4,596,812 | A | 6/1986 | Chidsey |
| 4,599,353 | A | 7/1986 | Bito |
| 4,621,100 | A | 11/1986 | Lund et al. |
| 4,704,386 | A | 11/1987 | Mueller |
| 4,757,089 | A | 7/1988 | Epstein |
| 4,812,457 | A | 3/1989 | Narumiya et al. |
| 4,883,819 | A | 11/1989 | Bito |
| 4,889,845 | A | 12/1989 | Ritter et al. |
| 4,952,581 | A | 8/1990 | Bito et al. |
| 4,968,812 | A | 11/1990 | Wang et al. |
| 5,001,153 | A | 3/1991 | Ueno |
| 5,041,439 | A | 8/1991 | Kasting et al. |
| 5,063,057 | A | 11/1991 | Spellman et al. |
| 5,166,178 | A | 11/1992 | Ueno et al. |
| 5,194,429 | A | 3/1993 | Ueno |
| 5,212,324 | A | 5/1993 | Ueno |
| 5,219,885 | A | 6/1993 | Frolich et al. |
| 5,280,018 | A | 1/1994 | Ritter et al. |
| 5,288,754 | A | 2/1994 | Woodward et al. |
| 5,296,504 | A | 3/1994 | Stjernschantz et al. |
| 5,302,617 | A | 4/1994 | Ueno |
| 5,312,832 | A | 5/1994 | Chan |
| 5,321,128 | A | 6/1994 | Stjernschantz et al. |
| 5,332,730 | A | 7/1994 | Chan |
| 5,340,813 | A | 8/1994 | Klein et al. |
| 5,352,708 | A | 10/1994 | Woodward et al. |
| 5,409,911 | A | 4/1995 | Tyler et al. |
| 5,422,368 | A | 6/1995 | Stjernschantz |
| 5,422,369 | A | 6/1995 | Stjernschantz |
| 5,422,371 | A | 6/1995 | Liao et al. |
| 5,426,115 | A | 6/1995 | Ueno et al. |
| 5,431,881 | A | 7/1995 | Palacios |
| 5,458,883 | A | 10/1995 | Epstein |
| 5,464,868 | A | 11/1995 | Frolich et al. |
| 5,480,900 | A | 1/1996 | DeSantis, Jr. et al. |
| 5,500,230 | A | 3/1996 | Nathanson |
| 5,508,303 | A | 4/1996 | Isogaya et al. |
| 5,510,383 | A | 4/1996 | Bishop |
| 5,516,652 | A | 5/1996 | Abramovitz et al. |
| 5,567,079 | A | 10/1996 | Felder |
| 5,576,315 | A | 11/1996 | Hallinan et al. |
| 5,578,618 | A | 11/1996 | Stjernschantz et al. |
| 5,578,640 | A | 11/1996 | Hanson |
| 5,578,643 | A | 11/1996 | Hanson |
| 5,587,391 | A | 12/1996 | Burk |
| 5,605,814 | A | 2/1997 | Abramovitz et al. |
| 5,605,931 | A | 2/1997 | Hanson |
| 5,607,978 | A | 3/1997 | Woodward et al. |
| 5,627,208 | A | 5/1997 | Stjernschantz et al. |
| 5,641,494 | A | 6/1997 | Cauwenbergh |
| 5,658,897 | A | 8/1997 | Burk |
| 5,663,203 | A | 9/1997 | Ekerdt et al. |
| 5,665,773 | A | 9/1997 | Klimko et al. |
| 5,670,506 | A | 9/1997 | Leigh et al. |
| 5,681,850 | A | 10/1997 | Frolich et al. |
| 5,688,819 | A | 11/1997 | Woodward et al. |
| 5,698,733 | A | 12/1997 | Hellberg et al. |
| 5,703,108 | A | 12/1997 | Cameron et al. |
| 5,716,609 | A | 2/1998 | Jain et al. |
| 5,719,140 | A | 2/1998 | Chandrakumar et al. |
| 5,741,810 | A | 4/1998 | Burk |
| 5,759,789 | A | 6/1998 | Abramovitz et al. |
| 5,770,759 | A | 6/1998 | Ueno et al. |
| 5,773,472 | A | 6/1998 | Stjernschantz |
| 5,792,851 | A | 8/1998 | Schuster et al. |
| 5,834,498 | A | 11/1998 | Burk |
| 5,840,847 | A | 11/1998 | Abramovitz et al. |
| 5,849,791 | A | 12/1998 | Stjernschantz et al. |
| 5,863,948 | A | 1/1999 | Epstein et al. |
| 5,869,281 | A | 2/1999 | Abramovitz et al. |
| 5,877,211 | A | 3/1999 | Woodward |
| 5,885,766 | A | 3/1999 | Mahe et al. |
| 5,885,974 | A | 3/1999 | Danielov |
| 5,889,052 | A | 3/1999 | Klimko et al. |
| 5,892,099 | A | 4/1999 | Maruyama et al. |
| 5,958,723 | A | 9/1999 | Abramovitz et al. |
| 5,972,965 | A | 10/1999 | Taniguchi et al. |
| 5,973,002 | A | 10/1999 | Frolich et al. |
| 5,977,173 | A | 11/1999 | Wos et al. |
| 5,985,597 | A | 11/1999 | Ford-Hutchinson et al. |
| 5,990,346 | A | 11/1999 | Kataoka et al. |
| 5,994,397 | A | 11/1999 | Selliah et al. |
| 6,013,823 | A | 1/2000 | Mamarella et al. |
| 6,025,375 | A | 2/2000 | Taniguchi et al. |
| 6,025,392 | A | 2/2000 | Selliah et al. |
| 6,030,959 | A | 2/2000 | Tremont et al. |
| 6,030,999 | A | 2/2000 | Stjemschantz et al. |
| 6,031,001 | A | 2/2000 | Stjemschantz et al. |
| 6,031,079 | A | 2/2000 | Ford-Hutchinson et al. |
| 6,037,364 | A | 3/2000 | Burk |
| 6,037,368 | A | 3/2000 | Podos et al. |
| 6,043,264 | A | 3/2000 | Ohtake et al. |
| 6,048,895 | A | 4/2000 | Wos et al. |
| 6,107,338 | A | 8/2000 | Wos et al. |
| 6,110,969 | A | 8/2000 | Tani et al. |
| 6,121,253 | A | 9/2000 | Han et al. |
| 6,124,344 | A | 9/2000 | Burk |
| 6,126,957 | A | 10/2000 | Epstein |
| 6,160,129 | A | 12/2000 | Burk |
| 6,169,111 | B1 | 1/2001 | Zinke et al. |
| 6,232,344 | B1 | 5/2001 | Feng |
| 6,262,105 | B1 | 7/2001 | Johnstone |
| 6,372,730 | B1 | 4/2002 | deLong et al. |
| 6,403,649 | B1 | 6/2002 | Woodward et al. |
| 6,410,780 | B1 | 6/2002 | deLong et al. |
| 6,444,840 | B1 | 9/2002 | deLong et al. |
| 6,451,859 | B1 | 9/2002 | deLong et al. |
| 6,534,082 | B1 | 3/2003 | Epstein |
| 6,548,535 | B2 | 4/2003 | Garcia et al. |
| 6,586,463 | B2 | 7/2003 | deLong et al. |
| 6,716,876 | B2 | 4/2004 | Burk |
| 6,894,175 | B1 | 5/2005 | deLong et al. |
| 7,070,768 | B2 | 7/2006 | Krauss |
| 7,074,942 | B2 | 7/2006 | deLong |
| 7,115,659 | B2 | 10/2006 | deLong |
| 7,288,029 | B1 | 10/2007 | Lyon |
| 7,388,029 | B2 | 6/2008 | deLong et al. |
| 7,407,987 | B2 | 8/2008 | deLong et al. |
| 2001/0047025 | A1 | 11/2001 | Garcia et al. |
| 2002/0013294 | A1 | 1/2002 | deLong et al. |
| 2002/0037914 | A1 | 3/2002 | deLong et al. |
| 2002/0044953 | A1 | 4/2002 | Michelet et al. |
| 2002/0146439 | A1 | 10/2002 | deLong et al. |
| 2002/0172693 | A1 | 11/2002 | deLong et al. |
| 2003/0083381 | A1 | 5/2003 | Kumagai et al. |
| 2003/0147823 | A1 | 8/2003 | Woodward et al. |
| 2003/0191173 | A1 | 10/2003 | Garcia et al. |
| 2003/0199590 | A1 | 10/2003 | Cagle |
| 2004/0157912 | A1 | 8/2004 | Old et al. |
| 2004/0167190 | A1 | 8/2004 | Stjernschantz et al. |
| 2004/0171596 | A1 | 9/2004 | Prokai et al. |
| 2005/0058614 | A1 | 3/2005 | Krauss |
| 2006/0121069 | A1 | 6/2006 | deLong et al. |
| 2006/0135609 | A1 | 6/2006 | Toone et al. |
| 2006/0247214 | A1 | 11/2006 | deLong et al. |
| 2007/0161699 | A1 | 7/2007 | Epstein et al. |

| | | | |
|---|---|---|---|
| 2007/0254920 | A1 | 11/2007 | deLong et al. |
| 2007/0282006 | A1 | 12/2007 | Woodward et al. |
| 2008/0070988 | A1 | 3/2008 | Woodward et al. |
| 2008/0103184 | A1 | 5/2008 | deLong et al. |
| 2008/0241078 | A1 | 10/2008 | deLong et al. |
| 2009/0018204 | A1 | 1/2009 | Brinkenhoff |
| 2009/0203659 | A1 | 8/2009 | Woodward et al. |
| 2009/0286769 | A1 | 11/2009 | delong et al. |
| 2010/0105771 | A1 | 4/2010 | deLong et al. |
| 2010/0105775 | A1 | 4/2010 | deLong et al. |

FOREIGN PATENT DOCUMENTS

| | | |
|---|---|---|
| DE | 2365101 | 7/1975 |
| DE | 24 60 990 | 7/1976 |
| DE | 2660990 | 7/1976 |
| DE | 2605584 | 8/1976 |
| DE | 2605242 | 9/1976 |
| DE | 2517771 | 10/1976 |
| DE | 2737808 | 3/1978 |
| EP | 0170258 | 2/1986 |
| EP | 249194 | 6/1986 |
| EP | 0295092 | 12/1988 |
| EP | 0308135 | 3/1989 |
| EP | 572014 | 1/1993 |
| EP | 639563 | 2/1995 |
| EP | 648488 | 4/1995 |
| EP | 1008588 | 2/1998 |
| EP | 857718 | 8/1998 |
| EP | 1016660 | 9/1998 |
| EP | 911321 | 4/1999 |
| EP | 925787 | 6/1999 |
| EP | 970697 | 9/1999 |
| EP | 947500 | 10/1999 |
| EP | 1159266 | 12/2001 |
| FR | 2108027 | 9/1971 |
| FR | 2182928 | 12/1973 |
| FR | 2239458 | 2/1975 |
| FR | 2314712 | 1/1977 |
| FR | 2730811 | 2/1995 |
| GB | 1236227 | 6/1971 |
| GB | 1251750 | 10/1971 |
| GB | 1285371 | 8/1972 |
| GB | 1285372 | 8/1972 |
| GB | 1456512 | 11/1976 |
| GB | 1456513 | 11/1976 |
| GB | 1456514 | 11/1976 |
| GB | 1456838 | 11/1976 |
| GB | 1542569 | 3/1979 |
| GB | 1545411 | 5/1979 |
| GB | 2048254 | 12/1980 |
| GB | 2330307 | 4/1999 |
| JP | 49-069636 | 7/1974 |
| JP | 49-093342 | 9/1974 |
| JP | 49-101356 | 9/1974 |
| JP | 49-102647 | 9/1974 |
| JP | 51-086449 | 7/1976 |
| JP | 52-053841 | 4/1977 |
| JP | 53-028160 | 3/1978 |
| JP | 58-029710 | 2/1983 |
| JP | 61-218510 | 9/1986 |
| JP | 02 022226 | 1/1990 |
| JP | 03034934 | 2/1991 |
| JP | 3-83925 | 4/1991 |
| JP | 3-83926 | 4/1991 |
| JP | 4-300833 | 10/1992 |
| JP | 5-331025 | 12/1993 |
| JP | 9-295921 | 11/1997 |
| JP | 10-251225 | 9/1998 |
| JP | 10-287532 | 10/1998 |
| JP | 2003180399 | 7/2003 |
| WO | 86/00616 | 1/1986 |
| WO | WO 89/03384 | 4/1989 |
| WO | 90/02553 | 3/1990 |
| WO | 92/02495 | 2/1992 |
| WO | 94/08585 | 4/1994 |
| WO | 95/00552 | 1/1995 |
| WO | 95/11003 | 4/1995 |
| WO | 95/11033 | 4/1995 |
| WO | 95/18102 | 7/1995 |
| WO | 95/19165 | 7/1995 |
| WO | 95/19964 | 7/1995 |
| WO | 96/10407 | 4/1996 |
| WO | 96/36599 | 11/1996 |
| WO | WO 96/36599 A1 | 11/1996 |
| WO | 97/03973 | 2/1997 |
| WO | 97/09049 | 3/1997 |
| WO | 97/15319 | 5/1997 |
| WO | 97/23223 | 7/1997 |
| WO | 97/23225 | 7/1997 |
| WO | 97/23226 | 7/1997 |
| WO | WO 97/23225 A1 | 7/1997 |
| WO | 97/29735 | 8/1997 |
| WO | 97/31895 | 9/1997 |
| WO | 97/39754 | 10/1997 |
| WO | 98/00100 | 1/1998 |
| WO | 98/12175 | 3/1998 |
| WO | 98/13016 | 4/1998 |
| WO | 98/19680 | 5/1998 |
| WO | 98/20880 | 5/1998 |
| WO | 98/20881 | 5/1998 |
| WO | 98/21180 | 5/1998 |
| WO | 98/21181 | 5/1998 |
| WO | 98/21182 | 5/1998 |
| WO | 98/27976 | 7/1998 |
| WO | 98/28264 | 7/1998 |
| WO | 98/33497 | 8/1998 |
| WO | 98/39293 | 9/1998 |
| WO | 98/47515 | 10/1998 |
| WO | 98/50024 | 11/1998 |
| WO | 98/53809 | 12/1998 |
| WO | 98/57930 | 12/1998 |
| WO | 98/57942 | 12/1998 |
| WO | 98/58911 | 12/1998 |
| WO | 99/02165 | 1/1999 |
| WO | 99/12550 | 3/1999 |
| WO | 99/12551 | 3/1999 |
| WO | 99/12552 | 3/1999 |
| WO | 99/12553 | 3/1999 |
| WO | 99/12554 | 3/1999 |
| WO | 99/12555 | 3/1999 |
| WO | 99/12556 | 3/1999 |
| WO | 99/12557 | 3/1999 |
| WO | 99/12558 | 3/1999 |
| WO | 99/12559 | 3/1999 |
| WO | 99/12560 | 3/1999 |
| WO | 99/12561 | 3/1999 |
| WO | 99/12563 | 3/1999 |
| WO | 99/12895 | 3/1999 |
| WO | 99/12896 | 3/1999 |
| WO | 99/12897 | 3/1999 |
| WO | 99/12898 | 3/1999 |
| WO | 99/12899 | 3/1999 |
| WO | WO 99/12550 A1 | 3/1999 |
| WO | WO 99/12551 A1 | 3/1999 |
| WO | WO 99/12895 A1 | 3/1999 |
| WO | WO 99/12896 A1 | 3/1999 |
| WO | WO 99/12899 A1 | 3/1999 |
| WO | 99/19300 | 4/1999 |
| WO | 99/21562 | 5/1999 |
| WO | 99/22731 | 5/1999 |
| WO | 99/25357 | 5/1999 |
| WO | 99/25358 | 5/1999 |
| WO | 99/30675 | 6/1999 |
| WO | 99/30718 | 6/1999 |
| WO | 99/32441 | 7/1999 |
| WO | 99/32640 | 7/1999 |
| WO | 99/32641 | 7/1999 |
| WO | 99/33794 | 7/1999 |
| WO | 99/47497 | 9/1999 |
| WO | 99/50241 | 10/1999 |
| WO | 99/50242 | 10/1999 |
| WO | 99/61029 | 12/1999 |
| WO | 99/64621 | 12/1999 |
| WO | 99/65303 | 12/1999 |
| WO | 99/65527 | 12/1999 |
| WO | 00/02450 | 1/2000 |
| WO | 00/03736 | 1/2000 |
| WO | 00/03980 | 1/2000 |

| | | |
|---|---|---|
| WO | 00/04898 | 2/2000 |
| WO | 00/04899 | 2/2000 |
| WO | 00/07627 | 2/2000 |
| WO | 00/09557 | 2/2000 |
| WO | 00/13664 | 3/2000 |
| WO | 00/15608 | 3/2000 |
| WO | 00/16760 | 3/2000 |
| WO | 00/51971 | 9/2000 |
| WO | 00/51979 | 9/2000 |
| WO | 00/51980 | 9/2000 |
| WO | WO 00/54810 | 9/2000 |
| WO | 01/10873 | 2/2001 |
| WO | 01/74307 | 10/2001 |
| WO | 01/74313 | 10/2001 |
| WO | 01/74314 | 10/2001 |
| WO | 01/74315 | 10/2001 |
| WO | 02/067901 | 9/2002 |
| WO | 03/051822 | 6/2003 |
| WO | 03/066008 | 8/2003 |
| WO | 03/077910 | 9/2003 |
| WO | 2006/047466 | 5/2006 |
| WO | 2007/125818 | 11/2007 |
| WO | 2007/127639 | 11/2007 |
| WO | WO 2009/011744 | 1/2009 |

OTHER PUBLICATIONS

Alm, A., "The potential of prostaglandin derivates in glaucoma therapy; prostaglandins and derivates," Curr. Opin. Opthalmol (1993) 4(11):44-50.

Alm et al., "Effects on intraocular pressure and side effects of 0.005% latanoprost applied once daily, evening or morning," Ophthalmology (1995) 102(12):1743-1752.

Al-Sereiti, M.R., et al., "Pharmacology of Rosemary (Rosmarinus Officinalis Linn.) and Its Therapeutic Potentials," Indian Journal of Experimental Biology, vol. 37, Feb. 1999, pp. 124-130.

Anonymous, "Alprostadil (nexmed):Alprox-TD, Befar, Femprox, Prostaglandin E1 (nexmed)," Drugs R&D (1999) 2(6):413-414.

Audoly, L.P. et al., "Identification of specific EP receptors responsible for the hemodynamic effects of PGE2," Am. J. Physiol. (1999) 46(3):H924-930.

Bartman, W., et al., "Leutolytic Prostaglandins Synthesis and Biological Activity", Prostaglandins, vol. 17, No. 2, pp. 301-311, 1979.

Bundy, G. L., and Lincoln, F. H., "Synthesis of 17-Phenyl-18, 19, 20-Trinoprostaglandins 1. The PG, Series," Prostaglandins, vol. 9, No. 1, (Jan. 1975), pp. 1-4.

Cayatte, A.J. et al., "The thromboxane A2 receptor antagonist S18886 decreases atheroschlerotic lesions and serum intracellular adhesion molecule-1 in the Apo E knockout mouse," Circulation (1998) 96:115.

Chen, J. et al., "AGN 191129: a neutral prostaglandin F-2 alpha (PGF2a) analog that lacks the mitogenic and uterotonic effects typical of FP receptor agonists," IOVS (1999) 40:3562-B420, p. S675.

Chyun, Y.S. et al., "Stimulation of bone formation by prostaglandin E2," Prostaglandins (1984) 27:97-103.

Clissold, D., "The potential for prostaglandin pharmaceuticals," Spec. Publ.—R. Soc. Chem. (1999) 244:115-129.

Coleman, R.A. et al., "VIII. International Union of Pharmacology. Classification of prostanoid receptors: properties, distribution, and structure of the receptors and their subtypes," Pharmacol. Rev. (1994) 46(2):205-229.

Coleman, R.A. et al., "Prostanoids and their receptors," Comprehensive Med. Chem., Membranes and Receptors (1990) 3:643-714.

Collins, P.W. et al., "Synthesis of therapeutically useful prostaglandin and prostacyclin analogs," Chem. Rev. (1993) 93:1533-1564.

Corsini, A. et al., "(5Z)-Carbacyclin discriminates between prostacyclin receptors coupled to adenylate cyclase in vascular smooth muscle and platelets," Br. J. Pharmacol. (1987) 90:255-261.

Dean, T.R. et al., "Improvement of optic nerve head blood flow after one-week topical treatment with travoprost (AL-06221) in the rabbit," IOVS (1999) 40(4):2688-B563, p. S509.

Delong, M.A., "Prostaglandin receptor ligands: recent patent activity," Drugs (2000) 3(9):1039-1052.

Del Toro, F. et al., "Characterization of prostaglandin E2 receptors and their role in 24,25-(OH)2D2-mediated effects on resting zone chondrocytes," J. Cell Physiol. (2000) 182(2):196-208.

Depperman, W.J., Jr., "Up-to-date scalp tonic," New Eng. J. Med. (1970) 283(2):1115.

Eisenberg, D.L. et al., "A preliminary risk-benefit assessment of latanoprost and unoprostone in open-angle glaucoma and ocular hypertension," Drug Safety (1999) 20(6):505-514.

Ellis, C. K., et al., "Metabolism of Prostaglandin $D_2$ in the Monkey," J. of Biological Chem., vol. 254, No. 10, pp. 4152-4163 (1979).

Fall, P. M., et al "Inhibition of Collagen Synthesis by Prostaglandins in the Immortalized Rat Osteoblastic Cell Line Pyla: Structure-Activity Relations and Signal Transduction Mechanisms," J. Bone Miner. Res. (1994) 9:1935-1943 (abstract).

Fitzpatrick, F. A., "Separation of Prostaglandins and Thromboxanes by Gas Chromatography with Glass Capillary Columns," Analytical Chemistry, vol. 50, No. 1, pp. 47-52, 1978.

Flisiak, R. et al., "Effect of misoprostol on the course of viral hepatitis B," Hepato-Gastroenterology (1997) 44(17):1419-1425.

Funk, C.D. et al., "Cloning and expression of a cDNA for the human prostaglandin E receptor EP1 subtype," J. Biol. Chem. (1993) 268:26767-26772.

Garadi, R. et al., "Travoprost: a new once-daily dosed prostaglandin for the reduction of elevated intraocular pressure," IOVS (1999) 40(4):4378-B181, p. S831.

Geng, L. et al., "Topical or systemic 16,16 dm-prostaglandin E2 or WR-2721 (WR-1065) protects mice and alopecia after fractionated irradiation," Int. J. Radiat. Biol. (1992) 61(4):533-537.

Geng, L., Malkinson, F.D., Hanson, W.R., "Misoprostol, A $PGE_1$ Analog that is Radioprotective for Murine Intestine and Hair, Induces Widely Different Cytokinetic Changes in these Tissues," Journal of Investigative Dermatology, 1996, vol. 106, No. 4, p. 858.

Griffin, B.W. et al., "AL-8810: a novel prostaglandin F2a analog with selective antagonist effects at the prostaglandin F2a (FP) receptor," J. Pharmacol. Exp. Ther. (1999) 290(3);1278-1284.

Hall, A., Smith, W. H. T., "Clinprost Teijin," Current Opinion in Cardiovascular, Pulmonary & Renal Investigation Drugs, 1999, 1(5), pp. 605-610.

Hallinan, E.A. et al., "Aminoacetyl moiety as a potential surrogate for diacylhydrazine group of SC-51089, a potent PGE2 antagonist, and its analogs," J. Med. Chem. (1996) 39:609-613.

Hanson, W.R. et al., "16,16 dm prostaglandin 2 protects from acute radiation-induced alopecia in mice," Clin. Res. (1988) 36(6):906a.

Hanson, W.R. et al., "Misoprostol, A PGE1 Analog that is Radioprotective for Murine Intestine and Hair, Induces Widely Different Cytokinetic Changes in these Tissues," J. Invest. Dermatol. (1996) 106(4):858.

Hanson, W.R. et al., "Subcutaneous or topical administration of 16,16 dimethyl prostaglandin E2 protects from radiation-induced alopecia in mice," Int. J. Radiat. Oncol. Biol. Phys. (1992) 23(2):333-337.

Hartke, J.R. et al., "Prostanoid FP agonists build bone in the ovariectomized rat," J. Bone Min. Res. (1999) 14(T326): S207.

Hayashi, M. et al., "Prostaglandin Analogues Possessing Antinidatory Effects. 1. Modification of the ω Chain," J. Med. Chem. (1980) 23(5):519-524.

Hecker, M. et al., "Studies on the interaction of minoxidil with prostacyclin synthase in-vitro," Biochem. Pharmacol. (1988) 37(17):3363-3365.

Houssay, A.B. et al., "Effects of prostaglandins upon hair growth in mice," Acta Physiol. Let. Am. (1976) 266(3):186-191.

Huang, A. et al., "Different modes of inhibition of increase in cytosolic calcium and aggregation of rabbit platelets by two thromboxane A2 antagonists," Asia Pacific Journal of Pharmacology (1994) 9:163-171.

Hulan, H.W. et al., "The development of dermal lesions and alopecia in male rats fed grapeseed oil," Can. J. Physiol. Pharmacol. (1976) 54(1):1-6.

Hulan, H.W. et al., "The effect of long-chain monoenes on prostaglandin E2 synthesis by rat skin," Lipids (1977) 12(7):604-609.

Ichikawa, E.A. et al., "Molecular aspects of the structures and functions of the prostaglandin E receptors," J. Lipid Mediators Cell Signaling (1996) 14:83-87.

Jakobsson, P.J. et al., "Membrane-associated proteins in elcosanoid and glutathione metabolism (MAPEG)—a widespread protein superfamily," Am J. Resp. Crit. Care Med. (2000) 161:S20-S24.
Jimenez, J.J. et al., "Stimulated monocyte-conditioned media protect for cytosine arabinoside-induced alopecia in rat," Clin. Res. (1990) 38(4):973a.
Johnstone, M.A., "Hypertrichosis and increased pigmentation of eyelashes and adjacent hair in the region of the ipsilateral eyelids of patients treated with unilateral topical latanoprost," Amer. J. Ophthal (1997) 544-547.
Johnstone, M.A., Brief latanoprost Rx induces hypertrichosis, IOVS (1998) 39(4):1180-B61.
Karim, S.M.M. et al., "Prostaglandins and human respiratory tract smooth muscle: structure activity relationship," Adv. Prostaglandin Thromboxane Res. (1980) 7:969-980.
Kende, et, al., "Prostaglandin Phosphonic Acids Through Homolytic Halodecarboxylation of Prostaglandins $F_{1\alpha}$ and $F_{2\alpha}$," Tetrahedron Letters, vol. 40, pp. 8189-8192 (1999).
Kerstetter, J.R. et al., "Prostaglandin F2 alpha-l-isopropylester lowers intraocular pressure without decreasing aqueous humor flow," Am. J. Ophthalmology (1988) 105:30-34.
Kiriyama, M. et al., "Ligand binding specificities of the eight types and subtypes of the mouse prostanoid receptors expressed in Chinese hamster ovary cells," Br. J. Pharm. (1997) 122:217-224.
Kluender, H.C. et al., "The Synthesis of Diethylphosphonoprostaglandin Analogs" Prostaglandins and Medicine (1979) 2(6):441-444.
Krauss, A.H.P. et al., "Evidence for human thromboxane receptor heterogeneity using a novel series of 9,11-cyclic carbonate derivatives of prostaglandin-F2-alpha," Br. J. Pharmacol. (1996) 117(6):1171-1180.
Kvedar, J.C. et al., "Topical minoxidil in the treatment of male pattern alopecia," Pharmacotherapy (1987) 7(6):191-197.
Lachgar, S. et al., "Effect of VEGF and minoxidil on the production of arachidonic acid metabolites by cultured hair, dermal papilla cells," Eur. J. Dermatol. (1996) 6(5):365-368.
Lachgar, S. et al., "Hair dermal papilla cell metabolism is influenced by minoxidil," Fundam Clin. Pharmacol. (1997) 11(2):178.
Lachgar, S. et al., "Modulation by minoxidil and VEGF of the production of inflammatory mediators by hair follicle dermal papilla cells," J. Invest. Derm. (1995) 104(1):161.
Lardy, C. et al., "Antiaggregant and antivasospastic properties of the new thromboxane A2 receptor antagonist sodium 4-[[1-[[[(4-chlorophenyl) sulfonyl]amino] methyl] cyclopentyl] methyl] benzeneacetate," Arzneim.-Forsch./Drug Res. (1994) 44(11):1196-1202.
Liljebris, C., Selen, G., Resul, B. Stjernschantz, J., and Hacksell, U., "Derivatives of 17-Phenyl-18, 19, 20 Trinorprostaglan $F_{2\alpha}$ Isopropyl Ester: Potential Antiglaucoma Agents," Journal of Medicinal Chemistry, vol. 38, No. 2, (1995), pp. 289-304.
Ling, G. et al., "16,16 dm prostaglandin E2 protects mice from fractionated radiation-induced alopecia," Clin. Res. (1990) 38(3):858a.
Lundy, M.W. et al., "Restoration of cancellous architecture and increased bone strength in aged osteopenic rats treated with fluprostenol, "J. Bone Min. Res. (1999) 1(4)SA368:S401.
Malkinson, F.D. et al., "Prostaglandins protect against murine hair injury produced by ionizing radiation or doxorubicin," J. Invest. Dermatol. (1993) 101(1, Suppl):135S-137S.
Maruyama, T. et al., "EP1 receptor antagonists suppress tactile allodynia in rats," Prostaglandins Lipid Mediat. (1999) 59:217.
Matsumura, H., "Prostaglandins and Sleep," Saishin No to Shinkai Kagaku Shiritzu 10, 1998, pp. 79-89 (no English translation available).
Maw, G.N., "Pharmacological therapy for the treatment of erectile dysfunction," Annu. Rep. Med. Chem. (1999) 34:71-80.
McCullough, P.A., "Ridogrel,"Current Opinion in Anti-inflammatory & Immunomodulatory Investigation Drugs (1999) 1(3):265-276.
Michelet, J.F. et al., "Activation of cytoprotective prostaglandin synthase-1 by minoxidil as a possible explanation for its hair growth-stimulation effect," J. Invest. Dermatol. (1997) 108(2):205-209.
Millikan, L.E., "Treatment of alopecia," J. Clin. Pharmacol. (1987) 27(9):715.
Millikan, L.E., "Treatment of male pattern baldness," Drug Therapy (1989) 19(3):62-73.
Miyamoto, T., et al., "A comparison in the Efficacy and Safety between Ramatroban (BAY u 3405) and Ozargrel HCl for Bronchial Asthma: A Phase III, Multi-Center, Randomized, Double-Blind, Group Comparative Study," 13, 1997, pp. 599-639 Abstract (in English).
Mori, S. et al., "Effects of prostaglandin E2 on production of new cancellous bone in the axial skeleton of overlectomized rats," Bone (1990) 11:103-113.
Murakami, T. et al., "Effect of isocarbacyclin methyl ester incorporated in lipid microspheres on experimental models of peripheral obstructive disease," Arzheim.-Forsh/Drug Res. (1995) 45(II)(9):991-994.
Narumiya, S., "Roles of prostanoids in health and disease, lessons from receptor-knockout mice," Int. Congr. Ser. (1999) 1181:261-269.
Negishi, M. et al., "Molecular mechanisms of diverse actions of prostanoid receptors," Biochimica et Biophysica Acta (1995) 1259:109-120.
Norridin, R.W. et al., "The role of prostaglandins in bone in vivo," Prostaglandins, Leukotrienes and Essential Fatty Acids (1990) 41:139-149.
Olsen, E.A. et al., "Transdermal viprostol in the treatment of male pattern baldness," J. Amer. Acad. Dermatol. (1990) 23(3 Part 1):470-472.
Orlicky, D.J., "Negative regulatory activity of a prostaglandin F2a receptor associated protein (FPRP)," Prostaglandins, Leukotrienes and Essential Fatty Acids (1996) 54(4):247-259.
Phamaprojects, No. 6321, Merck & Co. (2006) 1 page.
Rampton, D.S., Carty, E., Van Nueten, L., Anti-Inflammatory Profile in Vitro of Ridogrel, a Putative New Treatment for Inflammatory Bowel Disease, Gastroenterology, 1999, (116) G3477, p. 801.
Roenigk, H.H.,"New topical agents for hair growth," Clinics in Dermatology (1988) 6(4):119-121.
Roof, S.L. et al., "mRNA expression of prostaglandin receptors EP1, EP2, EP3 and EP4 in human osteoblast-like cells and 23 human tissues," J. Bone Min. Res. (1996) 11:S337.
Ruel, R. et al., "New class of biphenylene dibenzazocinones as potent ligands for the human EP1 prostanoid receptor," Bioorg. Med. Chem. Lett. (1999) 9:2699-2704.
Sakuma, Y. et al., "Crucial involvement of the PE4 subtype of prostaglandin E receptor in osteoclast formation by proinflammatory cytokines and lipopolysaccharide," J. Bone Min. Res. (2000) 15(2):218-227.
Sauk, J.J. et al., "Influence of prostaglandin E-1 prostaglandin E-2 and arachidonate on melanosomes in melanocytes and keratinocytes of anagen bulbs in-vitro," J. Invest. Dermatol. (1975) 64(5):332-337.
Sharif, N.A. et al., "3H AL-5848 ([3H]9 beta-(+)-fluprostenol). Carboxylic acid of travoprost (AL-6221), a novel FP prostaglandin to study the pharmacology and autoradiographic localization of the FP receptor," J. Phar. Pharmacol. (1999) 51(6):685-694.
Shih, M.S. et al., "PGE2 induces regional remodeling changes in Haversian envelope: a histomorphometric study of fractured ribs in beagles," Bone and Mineral (1986) 1:227-234.
Shimazaki, A., et al. "New Ethacrynic Acid Derivatives as Potent Cytoskeletal Modulators in Trabecular Meshwork Cells," Biol. Pharm. Bull. vol. 27, No. 6, 2004, pp. 846-850.
Shimazaki, A., et al., "Effects of the New Ethacrynic Acid Derivative SA9000 on Intraocular Pressure in Cats and Monkeys," Biol Pharm. Bull. vol. 27, No. 7, 2004, pp. 1019-1024.
Souillac, P. et al., "Characterization of delivery systems, differential scanning calorimetry," Encyclopedia of Controlled Drug Delivery, John Wiley & Sons (1999) 212-227.
Sredni, B. et al., "The protective role of the immunomodulator AS101 against chemotherapy-induced alopecia studies on human and animal models," Int. J. Cancer (1996) 65(1):97-103.
Tereda, N. et al., "Effect of a thromboxane A2 receptor antagonist, ramatroban (BAY U3405), on inflammatory cells, chemical mediators and non-specific nasal hyperactivity after allergen challenge in patients with perennial allergic rhinitis," Allergology Int. (1998) 47(1):59-67.

Tomita, Y. et al., "Melanocyte-stimulating properties of arachidonic acid metabolites: possible role in postinflammatory pigmentation," Pigm. Cell Res. (1992) 5(5, Pt. 2):357-361.
Ueda, K. et al., "Brief clinical and laboratory observations: coritical hyperostosis following long-term administration of prostaglandin E1 in infants with cyanotic congenital heart disease," J. Pediatrics (1980) 97:834-836.
Vandenburgh, A.M. et al., "A one-month dose-response study of AGN 192024, a novel antiglaucoma agent, in patients with elevated intraocular pressure," IOVS (1999) 40(4):4373-B176, p. S830.
Vayssairat, M., Preventive Effect of an Oral Prostacyclin Analog, Beraprost Sodium, on Digital Necrosis in Systemic Sclerosis, J. of Rheumatol., 1999, 26(10), pp. 2173-2178.
Vengerovsky, A.I. et al., "Hepatoprotective action of prostaglandins," Eksp. Klin Farmakof. (1997) 60(5):78-82.
Verbeuren, T., et al., "The TP-Receptor Antagonist S 18886 Unmasks Vascular Relaxation and Potentiates the Anti-Platelet Action of $PGD_2$," Journal of the International Society Thrombosis and Haemostasis, Jun. 6-12, 1997, p. 693.
Vincent, J.E., "Prostaglandin synthesis and selenium deficiency a hypothesis," Prostaglandins (1974) 8(4):339-340.
Vippagunta, "Crystalline solids," Adv. Drug Del. Rev. (2001) 48:3-26.
Voss, N.G. et al., "Induction of anagen hair growth in telogen mouse skin by topical latanoprost application," IOVS (1999) 40:3570-B428, p. S676.
Waddell, K. A., et al., "Combined Capillary Column Gas Chromatography Negative Ion Chemical Ionization Mass Spectrometry of Prostanoids," Biomed. Mass Spectrom., vol. 10, No. 2, pp. 83-88 (1983).
Wand, M., "Latanoprost and hyperpigmentation of eyelashes," Archives of Ophthalmology (1997) 115(9):1206-1208.
Wang, Y. et al., "The design and synthesis of 13, 14-dihydro prostaglandin F1a analogs as potent and selective ligands for the human FP receptor," J. Med. Chem. (2000) 43(5):945-952.
Watson et al., "A six-month, randomized, double-masked study in comparing latanoprost with timolol in open-angle glaucoma and ocular hypertension," Ophthalmology (1996) 103:126-137.
Woodward, D.F. et al., "Emerging evidence for additional prostanoid receptor subtypes," Curr. Top. Pharmacol. (1998) 4:153-163.
Woodward, D.F. et al., "Molecular characterization and ocular hypotensive properties of the prostanoid EP2 receptor," J. Oc. Pharm. Therap. (1995) 11(3):447-454.
Woodward, D.F. et al., "Studies on the ocular effects of a pharmacologically novel agent prostaglandin F2 alpha 1-OCH3 (AGN 191129) N-S," Arch. Pharmacol. (1998) 358(1):P1713.
Yoshida, K. et al., "Synthesis and pharmacological activities of the new TXA2 receptor antagonist Z-335 and related compounds," AFMC (1995) 95:53.
Zimbric, M.L. et al., "Effects of latanoprost of hair growth in the bald scalp of stumptailed macaques," IOVS (1999) 40:3569-B427, p. S676.
International Search Report for Application No. PCT/US00/05301 (WO 00/51980) dated Jul. 21, 2000 (3 pages).
Written Opinion for Application No. PCT/US00/05301 (WO 00/51980) dated Oct. 20, 2000 (7 pages).
International Preliminary Examination Report for Application No. PCT/US00/05301 (WO 00/51980) dated Mar. 16, 2001 (6 pages).
International Search Report for Application No. PCT/US00/20851 (WO 01/10873) dated Nov. 7, 2000 (4 pages).
Written Opinion for Application No. PCT/US00/20851 (WO 01/10873) dated Jul. 10, 2001 (9 pages).
International Preliminary Examination Report for Application No. PCT/US00/20851 (WO 01/10873) dated Oct. 12, 2001 (8 pages).
International Search Report for Application No. PCT/US98/18339 (WO 99/12895) dated Dec. 3, 1998 (2 pages).
International Preliminary Examination Report for Application No. PCT/US98/18339 (WO 99/12895) dated Jun. 28, 1999 (4 pages).
International Search Report for Application No. PCT/US98/18340 (WO 99/12896) dated Dec. 8, 1998 (3 pages).
Written Opinion for Application No. PCT/US98/18340 (WO 99/12896) dated Aug. 2, 1999 (7 pages).
International Preliminary Examination Report for Application No. PCT/US98/18340 (WO 99/12896) dated Dec. 6, 1999 (7 pages).
International Search Report for Application No. PCT/US98/18594 (WO 99/12898) dated Dec. 3, 1998 (3 pages).
Written Opinion for Application No. PCT/US98/18594 (WO 99/12898) dated May 25, 1999 (5 pages).
International Preliminary Examination Report for Application No. PCT/US98/18594 (WO 99/12898) dated Sep. 7, 1999 (5 pages).
International Search Report for Application No. PCT/IB99/00478 (WO 99/50241) dated Jul. 12, 1999 (3 pages).
Written Opinion for Application No. PCT/IB99/00478 (WO 99/50241) dated Feb. 21, 2004 (4 pages).
International Preliminary Examination Report for Application No. PCT/IB99/00478 (WO 99/50241) dated Jun. 23, 2000 (5 pages).
International Search Report for Application No. PCT/IB99/00480 (WO 99/50242) dated Jun. 25, 1999 (3 pages).
Written Opinion for Application No. PCT/IB99/00480 (WO 99/50242) dated Jan. 18, 2000 (6 pages).
International Search Report for Application No. PCT/US00/05299 (WO 99/51979) dated Jul. 28, 2000 (3 pages).
Written Opinion for Application No. PCT/US00/05299 (WO 99/51979) dated Oct. 20, 2000 (7 pages).
International Preliminary Examination Report for Application No. PCT/US00/05299 (WO 99/51979) dated Mar. 16, 2001 (7 pages).
International Search Report for Application No. PCT/US01/10368 (WO 01/74313) dated Nov. 7, 2001 (3 pages).
International Preliminary Examination Report for Application No. PCT/US01/10368 (WO 01/74313) dated Jun. 14, 2002 (2 pages).
International Search Report for Application No. PCT/US01/10369 (WO 01/74314) dated Nov. 7, 2001 (3 pages).
International Preliminary Examination Report for Application No. PCT/US01/10369 (WO 01/74314) dated Jun. 14, 2001 (3 pages).
International Search Report for Application No. PCT/US01/10370 (WO 01/74315) dated Nov. 7, 2001 (3 pages).
International Preliminary Examination Report for Application No. PCT/US01/10370 (WO 01/74315) dated Jun. 14, 2002 (2 pages).
International Search Report for Application No. PCT/US01/10547 (WO 01/74307) dated Jan. 2, 2002 (2 pages).
International Preliminary Examination Report for Application No. PCT/US01/10547 (WO 01/74307) dated Jun. 14, 2002 (2 pages).
United States Office Action for U.S. Appl. No. 09/946,021 dated Jan. 15, 2002 (5 pages).
United States Office Action for U.S. Appl. No. 09/946,021 dated May 24, 2002 (4 pages).
United States Office Action for U.S. Appl. No. 09/946,021 dated Oct. 15, 2002 (4 pages).
United States Office Action for U.S. Appl. No. 11/174,420 dated Aug. 20, 2007 (8 pages).
United States Office Action for U.S. Appl. No. 11/174,420 dated Dec. 5, 2008 (6 pages).
United States Office Action for U.S. Appl. No. 11/174,420 dated Jul. 22, 2009 (5 pages).
United States Office Action for U.S. Appl. No. 11/174,420 dated Feb. 3, 2010 (6 pages).
United States Patent Office Action for U.S. Appl. No. 11/174,420 dated Feb. 3, 2010 (6 pages).
United States Patent Office Action for U.S. Appl. No. 12/479,532 dated Oct. 6, 2009 (5 pages).
United States Office Action for U.S. Appl. No. 09/148,006 dated Jan. 29, 1999 (3 pages).
United States Office Action for U.S. Appl. No. 09/148,374 dated Feb. 11, 1999 (4 pages).
United States Office Action for U.S. Appl. No. 09/148,374 dated May 28, 1999 (3 pages).
United States Office Action for U.S. Appl. No. 09/148,374 dated Oct. 1, 1999 (3 pages).
United States Office Action for U.S. Appl. No. 09/148,374 dated Jan. 11, 2000 (4 pages).
United States Office Action for U.S. Appl. No. 09/148,538 dated Apr. 8, 1999 (6 pages).
United States Office Action for U.S. Appl. No. 09/647,381 dated Sep. 20, 2001 (8 pages).

United States Office Action for U.S. Appl. No. 09/647,380 dated Sep. 18, 2001 (8 pages).
United States Office Action for U.S. Appl. No. 09/914,531 dated Dec. 7, 2001 (5 pages).
United States Office Action for U.S. Appl. No. 09/774,555 dated Jul. 9, 2002 (8 pages).
United States Office Action for U.S. Appl. No. 09/774,555 dated May 23, 2005 (7 pages).
United States Office Action for U.S. Appl. No. 09/774,555 dated Jan. 6, 2006 (6 pages).
United States Office Action for U.S. Appl. No. 09/774,555 dated Aug. 31, 2006 (9 pages).
United States Office Action for U.S. Appl. No. 11/565,297 dated Jul. 12, 2007 (5 pages).
United States Office Action for U.S. Appl. No. 11/565,297 dated Jul. 31, 2007 (5 pages).
United States Patent Office Action for U.S. Appl. No. 12/138,733 dated Nov. 24, 2009 (10 pages).
United States Office Action for U.S. Appl. No. 09/774,558 dated Apr. 25, 2002 (13 pages).
United States Office Action for U.S. Appl. No. 09/774,558 dated Apr. 15, 2003 (11 pages).
United States Office Action for U.S. Appl. No. 09/774,558 dated Dec. 4, 2003 (11 pages).
United States Office Action for U.S. Appl. No. 09/774,558 dated Nov. 5, 2004 (6 pages).
United States Office Action for U.S. Appl. No. 09/774,558 dated Mar. 28, 2006 (8 pages).
United States Office Action for U.S. Appl. No. 11/476,246 dated Jul. 22, 2009 (9 pages).
United States Office Action for U.S. Appl. No. 09/774,557 dated Mar. 5, 2003 (9 pages).
United States Office Action for U.S. Appl. No. 09/774,557 dated Nov. 26, 2004 (10 pages).
United States Office Action for U.S. Appl. No. 11/138,097 dated Jul. 16, 2007 (1 page).
United States Office Action for U.S. Appl. No. 11/967,423 dated Feb. 4, 2009 (10 pages).
United States Patent Office Action for U.S. Appl. No. 12/535,513 dated Dec. 18, 2009 (10 pages).
United States Office Action for U.S. Appl. No. 09/774,556 dated Mar. 19, 2002 (11 pages).
United States Office Action for U.S. Appl. No. 09/774,556 dated May 14, 2003 (2 pages).
United States Office Action for U.S. Appl. No. 09/774,556 dated Mar. 23, 2004 (10 pages).
United States Office Action for U.S. Appl. No. 09/774,556 dated Dec. 14, 2004 (5 pages).
United States Office Action for U.S. Appl. No. 09/774,556 dated Jul. 18, 2005 (6 pages).
United States Office Action for U.S. Appl. No. 11/334,689 dated Aug. 25, 2009 (11 pages).
Australian Patent Office Action dated Jul. 3, 2002 (2 pages) for Australian Patent No. 766163 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Australian Patent Office Action dated Jul. 8, 2003 (2 pages) for Australian Patent No. 766163 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated Jul. 27, 2004 (2 pages) for Canadian Patent No. 2364948 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated Nov. 1, 2006 (2 pages) for Canadian Patent No. 2364948 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated Oct. 30, 2007 (3 pages) for Canadian Patent No. 2364948 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated Sep. 4, 2008 (2 pages) for Canadian Patent No. 2364948 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated Aug. 6, 2009 (2 pages) for Canadian Patent No. 2364948 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
European Patent Office Action dated May 30, 2003 (2 pages) for European Patent No. 1159266 (also cited separately on the enclosed 1449A), claiming priority to International Application No. PCT/US00/05301 (WO 00/51980) filed Feb. 29, 2000 and U.S. Appl. No. 60/122,924, filed Mar. 5, 1999.
Canadian Patent Office Action dated May 31, 2010 (1 page) for Canadian Patent No. 2364948, claiming priority to International Application No. PCT/US00/05301 (WO 00/51980) filed Feb. 29, 2000 and U.S. Appl. No. 60/122,924, filed Mar. 5, 1999.
Japanese Patent Office Action dated Apr. 16, 2010 (7 pages) for Japanese Patent No. 2000-602208, claiming priority to International Application No. PCT/US00/05301 (WO 00/51980) filed Feb. 29, 2000 and U.S. Appl. No. 60/122,924, filed Mar. 5, 1999.
United States Patent Office Action for U.S. Appl. No. 11/334,689 dated Apr. 30, 2010 (11 pages).
United States Patent Office Action for U.S. Appl. No. 11/476,246 dated Apr. 19, 2010 (7 pages).
United States Patent Office Notice of Allowance for U.S. Appl. No. 12/535,513 dated Jun. 3, 2010 (5 pages).
United States Patent Office Notice of Allowance for U.S. Appl. No. 12/138,733 dated Jun. 3, 2010 (5 pages).
Japanese Patent Office Action dated Dec. 3, 2010 (6 pages) for Japanese Patent No. 2000-602208, claiming priority to International App. No. PCT/US00/05301 (WO 00/51980) filed Feb. 29, 2000 and U.S. Appl. No. 60/122,924, filed Mar. 5, 1999.
U.S. Appl. No. 90/009,430, filed Mar. 15, 2009, Woodward.
U.S. Appl. No. 90/009,431, filed Mar. 10, 2009, Johnstone.
"Agents for Glaucoma," Journal of the American Pharmaceutical Association, New Drugs of 2001, http://www.edscape.com/viewarticle/436631_22 (2007) 4 pages.
"Bimatoprost (ophthalmic)" Medlineplus, Health information online (Jul. 24, 2001) 4 pages, www.nlm.nih.gov/medlineplus/druginfor/uspdi/500295.
Letter from Bernice Tao at Apotex, Inc. to the General Counsels at Allergan, Inc. and Duke University regarding "Apotex Bimatoprost Topical Solution 0.03% Paragraph IV Certification—U.S. Patent Nos. 7,351,404 and 7,388,029" (Jul. 26, 2010) 49 pages.
Allergan Press Release, "Phase III Lumigan? (AGN 192024) data presented at American Academy of Ophthalmology," Mar. 1, 2000, 5 pages.
Alm, A. et al., "Phase III latanoprost studies in Scandanavia, the United Kingdom and the United States," Surv. Ophthalmol. (1997) 41(Suppl 2):S105-S110.
Alm, A. et al., "Uveoscleral outflow—a review," Exp. Eye Res. (2009) 88(4):760-768, Epub Jan. 3, 2009.
Bean, G.W., "Commercially available prostaglandin analogs for the reduction of intraocular pressure: similarities and differences," Survey of Ophthalmology (2008) 53(1):S69-84.
Berglund, B.A. et al., "Investigation of structural analogs of prostaglandin amides for binding to and activation of CB1 and CB2 cannabinoid receptors in rat brain and human tonsils," Adv. Exp. Med. Biol. (1999) 469:527-533.
Bito, L., "A new approach to the medical management of glaucoma, from the bench to the clinic, and beyond," The Proctor Lecture (2001) 42(6):1126-1133.

Bito, L.Z. et al., "Long-term maintenance of reduced intraocular pressure by daily or twice daily topical application of psotaglandins to cat or rhesus monkey eyes," Invest. Ophthalmol. Vis. Sci. (1983) 24(3):312-319.
Brandt, J.D. et al., "Comparison of once-or twice-daily bimatoprost with twice-daily timolol in pateints with elevated IPO. A three month clinical tril," Ophthalmology (2001) 108(6):1023-1031.
Cadet, P. et al., "Molecular identification and functional expression of mu3, a novel alternatively apliced variant of the human mu opiate receptor gene," J. Immunol. (2003) 170(10):5118-5123.
Camras, C.B. et al., "Latanoprost, a prostaglandin analog, for glaucoma therapy," Ophthalmology (1996) 103(11):1916-1924.
Camras, C.B. et al., "Multiple dosing of prostaglandin F2alpha or epinephrine on cynomolgus monkey eyes," Invest. Ophthalmol. Vis. Sci. (1987) 28(3):463-469.
Camras, C.B. et al., "Multiple dosing of prostaglandin F2alpha or epinephrine on cynomolgus monkey eyes," Invest. Ophthalmol. Vis. Sci. (1988) 29(9):1428-1436.
Camras, C.B. et al., "Reduction of intraocular pressure in normal and glaucomatous primate (Aotus trivirgatus) eyes by topically applied prostaglandin F2alpha," Curr. Eye Res. (1981) 1(4):205-209.
Camras, C.B. et al., "Multiple dosing of prostaglandin F2alpha or epinephrine on cynomolgus monkey eyes," Invest. Ophthalmol. Vis. Sci. (1987) 28(6):921-926.
Camras, C.B. et al. "Bimatoprost, the prodrug of a prostaglandin analogue," Br. J. Ophthalmol. (2008) 92:862-863.
Camras, C.B., "Comparison of latanoprost and timolol in patients with ocular hypertension and glaucoma," Ophthalmology (1996) 103(1):138-147.
Camras, C.B., "Detection of the free acid of bimatoprost in aqueous humor samples from human eyes treated with bimatoprost before cataract surgery," American Academy of Ophthalmology (2004) 2193-2198.
Cantor, L.B. et al., "Levels of bimatoprost acid in the aqueous humour after bimatoprost treatment of patients with cataract," Br. J. Ophthalmol. (2007) 91:629-632.
Cantor, L.B., "Reply—bimatoprost, the prodrug of a prostaglandin analogue," Br. J. Ophthalmol. (2008) 92:863-864.
CAS RN 155206-00-1 (May 20, 1994).
Center for Drug Evaluation and Research, "Medical Officer's Review of NDA, Application No. 21-275," Mar. 14, 2001; 120-day safety update Jan. 23, 2001; Mar. 2, 2001; Sep. 18, 2000, 63 pages.
Crowston, J.G. et al., "Effect of bimatoprost on intraocular pressure in prostaglandin FP receptor knockout mice," Invest. Ophthal. Vis. Sci. (2005) 46:4571-4577.
Darnell, J. et al., "Cell-to-cell signaling: hormones and receptors," Mol. Cell. Biol. (1990) 738-743.
Davies, S.S., "Hydrolysis of bimatoprost (lumigan) to its free acid by ocular tissue in vitro," J. Ocular Pharm. Thera. (2003) 19(1):45-54.
DuBiner, H. et al., "Efficacy and safety of bimatoprost in patients with elevated intraocular pressure: a 30-day comparison with latanoprost," Survey of Ophthal. (2001) 45(S4):S353-S360.
Fagot, D. et al., "Mitogenic signaling by prostaglandins in chemically transformed mouse fibroblasts: comparison with phorbol esters and insulin," Endocrinology (1993) 132(4):1729-1734.
Faulkner, R., "Aqueous humor concentrations of bimatoprost free acid, bimatoprost and travoprost free acid in cataract surgical patients administered multiple topical ocular doses of LUMIGAN® or TRAVATAN®," J. Ocular Pharm. Thera. (2010) 26(2):147-156.
FDA Label for Approved NDA 22-184—Lumigan 0.01% and Lumigan 0.03% (Aug. 31, 2010) 5 pages.
FDA Press Release, "FDA News" of Mar. 16, 2001 entitled "FDA approves two new intraocular pressure lowering drugs for the management of glaucoma," 2 pages.
Fiscella, R.G., "Peek into the drug pipeline," Review of Optometery Online, Jan. 15, 2001, pp. 1-5.
Frenkel, R.E. et al., "Evaluation of circadian control of intraocular pressure after a single drop of bimatoprost 0.03% or travoprost 0.004%," Curr. Med. Res. Opin. (2008) 24(4):919-923, epub Feb. 8, 2008.
Gandolfini, S. et al., "Three-month comparison of bimatoprost and latanoprost in patients with glaucoma and ocular hypertension," Adv. In Therapy (2001) 18(3):110-121.
Gerth, J. et al., "Drug makers reap profits on tax-backed research," New York Times, Apr. 23, 2000, 10 pages.
Giuffre, G., "The effects of prostaglandin F2alpha in the human eye," Graefe's Arch. Clin. Exp. Ophthalmol. (1985) 222:139-141.
Hellberg, M.R. et al., "The hydrolysis of the prostaglandin analog prodrug bimatoprost to 17-phenyltrinor PGF2a by human and rabbit ocular tissue," J. Ocular Pharmacol. Ther. (2003) 19:97-103.
Jimenez de Asua, L. et al., "The stimulation of the initiation of DNA synthesis and cell division in Swiss mouse 3T3 cells by prostaglandin F2alpha requires specific functional groups in the molecule," J. Biol. Chem. (1983) 256(14): 8774-8780.
Jordan, B.A. et al., "G-protein coupled receptor heterodimerization modulates receptor function," Nature (1999) 399(6737):697-700.
Kaufman, P.L., "Effects of intracamerally infused prostaglandins on outflow facility in cynomolgus monkey eyes with intact or retrodisplaced ciliary muscle," Exp. Eye Res. (1986) 43:819-827.
Lee, P.-Y. et al., "The effect of prostaglandin F2alpha on intraocular pressure in mormotensive human subjects," Invest. Ophthalmol. Vis. Sci. (1988) 29(10):1474-1477.
Liang, Y. et all., "Identification and pharmacological characterization of the prostaglandin FP receptor and FP receptor varian complexes," Br. J. Pharmacol. (2008) 154:1079-1093.
Lumigan 6-month phase 3 data presented at American Glaucoma Society Meeting, Mar. 2, 2001, Business Wire, 3 pages.
Maxey, K.M., "The hydrolysis of bimatoprost in corneal tissue generates a potent prostanoid FP receptor agonist," Survey of Ophthalmology (2002) 47(1):S34-40.
Mishima, H.K. et al., "A comparison of latanoprost and timolol in primary open-angle glaucoma and ocular hypertension," Arch. Ophthalmol. (1996) 114:929-932.
Ortonne, J-P. et al., "Hair melanin's and hair color: ultrastructural and biochemical aspects," J. Soc. Inv. Derm. (1993) 82S-89S.
Pfeiffer, N., "New developments in glaucoma drug therapy," Ophthalmologist (1992) 89:W1-W13.
Poyer, J.F. et al., "Prostaglandin F2 alpha effects on isolated rhesus monkey ciliary muscle," Invest. Ophthalmol. Vis. Sci. (1995) 36(12):2461-2465.
Response from the Food and Drug Administration to Pfizer's Citizen Petition and a Supplement (Aug. 31, 2010) at 23 (Exhibit 5), 26 pages.
Resul, B. et al., "Phenyl-substituted prostaglandins: potent and selective antiglaucoma agents," J. Med. Chem. (1993) 36(2):243-248.
Romano, M.R., "Evidence for the involvement of cannabinoid CB1 receptors in the bimatoprost-induced contractions on the human isolated ciliary muscle," Invest. Opthal. Vis. Sci. (2007) 48(8):3677-3682.
Sharif, N. A. et al., "Bimatoprost and its free acid are prostaglandin FP receptor agonists," Eur. J. Pharmacol. (2001) 432(2-3):211-213.
Sharif, N.A. et al., "Cat iris sphincter smooth-muscle contraction: comparison of FP—class prostaglandin analog agonist activities," J. Ocul. Pharmacol. Ther. (2008) 24(2):152-163.
Sharif, N.A. et al., "Human ciliary muscle cell responses to FP—class prostaglandin analogs: phosphoinositide hydrolysis, intracellular Ca2+ mobilization and MAP kinase activation," J. Ocul. Pharmacol. Ther. (2003) 19:437-455.
Sharif, N.A. et al., "Human trabecular meshwork cell responses induced by bimatoprost, travoprost, unoprostone, and other FP prostaglandin receptor agonist analogues," Invest. Ophthalmol. Vis. Sci. (2003) 44:715-721.
Sharif, N.A., "Ocular hypotensive FP prostaglandin (PG) analogs: PG receptor subtype binding affinities and selectivities, and agonist potencies at FP and other PG receptors in cultured cells," J. Ocular Pharm. Thera. (2003) 19(6):501-515.
Sharif, N.A., "Update and commentary on the pro-drug bimatoprost and a putative 'prostamide receptor'," Expert Rev. Ophthalmol. (2009) 4(5):477-489.
Sherwood, M. et al., "Six-month comparison of bimatoprost once-daily and twice-daily with timomol twice-daily in patients with elevated intraocular pressure," Surv. Ophthal. (2001) 45(4):S361-S368.
Sjoquist, B. et al., "Ocular and systemic pharmacokinetics of latanoprost in humans," Surv. Ophthalmol. (2002) 47(Supp 1):S6-12.

Sjoquist, B. et al., "Pharmacokinetics of latanoprost in the cynomolgus monkey. 3rd communication: tissue distribution after topical administration on the eye studied by whole body autoradiography, Glacoma research laboratories," Arzneimittelforschung (1999) 49:240-249.
Spada, C.S. et al., "Bimatoprost and prostaglandin F(2 alpha) selectively stimulate intracellular calcium signaling in different cat iris sphincter cells," Exp. Eye Res. (2005) 80(1):135-145.
Stamer, W.D. et al., "Cellular basis for bimatoprost effects on human conventional outflow," Invest. Ophthalmol. Vis. Sci. (2010) 51(10):5176-5181, Epub Apr. 30, 2010.
Stjernschantz, J. et al., "Phenyl substituted prostaglandin analogs for glaucoma treatment," Drugs of the Future (1992) 17(8):691-704.
Stjernschantz, J., "Studies on ocular inflammation and development of a prostaglandin analogue for glaucoma treatment," Exp. Eye Res. (2004) 78(4):759-766.
Stjernschantz, J.W., "From PGF2alpha-isopropyl ester to latanoprost: a review of the development of Xalatan: the Proctor lecture," Invest. Ophthalmol. Vis. Sci. (2001) 42(6):1134-1145.
The Newsletter of the Glaucoma Foundation, Fall 2000, vol. 11, No. 2, 11 pages.
Van Alphen, G.W.H.M. et al., "The effect of prostaglandins on the isolated internal muscles of the mammalian eye, including man," Documenta Ophthalmologica (1977) 42(2):397-415.
Vielhauer, G.A. et al., "Cloning and localization of hFP(S): a six-transmembrane mRNA splice variant of the human FP prostanoid receptor," Arch. Biochem. Biophys. (2004) 421(2):175-185.
Villumsen, J. et al., "Prostaglandin F2alpha-isopropylester eye drops: effect on intraocular pressure in open-angle glaucoma," Br. J. Ophthalmol. (1989) 73:975-979.
White, J.H. et al., "Heterodimerization is required for the formation of a functional GABA(B) receptor," Nature (1998) 396(6712):679-682.
Wilson, S.J. et al., "Dimerization of the human receptors for prostacyclin and thromboxane facilitates thromboxane receptor-mediated cAMP generation," J. Biol. Chem. (2004) 279(51):53036-53047.
Woodward, D., "Replacement of carboxylic acid group of prostaglandin F2a with a hydroxyl or methoxy substituent provides biologically unique compounds," Br. J. Pharma. (2000) 130(8):1933-1943.
Woodward, D.F. et al., "Bimatoprost effects on aqueous humor dynamics in monkeys," J. Ophthalmol. (2010) Article ID 926192, 5 pages.
Woodward, D.F. et al., "Bimatoprost: a novel antiglaucoma agent," Cardiovasc. Drug Rev. (2004) 22(2):103-120.
Woodward, D.F. et al., "Identification of an antagonist that selectively blocks the activity of prostamides (prostaglandin-ethanolamides) in the feline iris," Br. J. Pharmacol. (2007) 150:342-352.
Woodward, D.F. et al., "Pharmacological characterization of a novel anti-glaucoma agent," J. Pharmacol. Exp. Ther. (2003) 305:772-785.
Woodward, D.F. et al., "The pharmacology of bimatoprost (Lumigan)," Surv. Ophthalmol. (2001) 45(Suppl 4):S337-45.
Yamaji, K. et al., "Prostaglandins E1 and E2, but not F2alpha or latanoprost, inhibit monkey ciliary muscle contraction," Curr. Eye Res. (2005) 30(8):661-665.
Zeigler, T., "Old drug, new use: new research shows common cholesterol-lowering drug reduces multiple sclerosis symptoms in mice," Natl. Institute of Neurological Disorders and Stroke (2003) 2 pages.
United States Patent Office Action for U.S. Appl. No. 12/535,513 dated Mar. 3, 2011 (8 pages).
United States Patent Office Action for U.S. Appl. No. 12/138,733 dated Feb. 23, 2011 (8 pages).
United States Patent Office Notice of Allowance for U.S. Appl. No. 11/174,420 dated Jan. 12, 2011 (5 pages).
Higginbotham, E.J. et al., "One-year randomized study comparing bimatoprost and timololin in glaucoma and ocular hypertension," Arch. Ophthal. (2002) 120(10):1286-1293.
United States Patent Office Action for U.S. Appl. No. 12/260,522 dated May 25, 2011 (14 pages).
United States Patent Office Action for U.S. Appl. No. 12/260,534 dated Nov. 18, 2011 (8 pages).
Bundy et al., "Synthesis of 17-Phenyl-18,19,20-trinorprostaglandins I. The Pg, Series", *Prostaglandins,* 1975, pp. 1-4, vol. 9, No. 1.
Bartman et al., "Synthesis and Biological Activity", *Prostaglandins,* 1979, pp. 301-311, vol. 17, No. 2.
Liljebris et al., "Derivatives of 17-Phenyl-18,19,20-trinor-prostaglandin $F_{2\alpha}$Isopropyl Ester: Potential Antigalucoma Agents", *J. Med. Chem.,* 1995, pp. 289-304, vol. 38, No. 2.

C16 UNSATURATED FP-SELECTIVE PROSTAGLANDINS ANALOGS

Matter enclosed in heavy brackets [ ] appears in the original patent but forms no part of this reissue specification; matter printed in italics indicates the additions made by reissue.

CROSS REFERENCE

This is a *reissue of U.S. Pat. No. 6,586,463 and also a continuation reissue application of Reissue application Ser. No. 11/174,420. More than one reissue application has been filed for the reissue of U.S. Pat. No. 6,586,463. The reissue applications are application Ser. Nos. 12/479,532* (*which is the present application*) *and 11/174,420* (*which is abandoned*), *both of which are reissues of U.S. Pat. No. 6,586,463. Re. application Ser. No. 11/174,420, filed Jul. 1, 2005 now abandoned, is a reissue application of application Ser. No. 09/946,021, filed Sep. 4, 2001, now U.S. Pat. No. 6,586,463, which is a* continuation under 35 U.S.C. §120 of PCT International Application Ser. No. PCT/US00/05301, filed Feb. 29, 2000; which claims priority to Provisional Application Ser. No. 60/122,924, filed Mar. 5, 1999.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_2$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_2$ has the following formula:

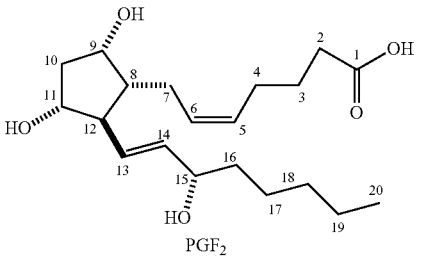

$PGF_2$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", Chem. Rev. Vol. 93 (1993), pp. 1533-1564; G. L. Bundy and F. H. Lincoln, "Synthesis of 17-Phenyl-18,19,20-Trinorprostaglandins: I. The $PG_1$ Series", Prostaglandins, Vol. 9 No. 1 (1975), pp. 1-4; W. Bartman, G. Beck, U. Lerch, H. Teufel, and B. Scholkens, "Luteolytic Prostaglandins: Synthesis and Biological Activity", Prostaglandins, Vol. 17 No. 2 (1979), pp. 301-311; C. liljebris, G. Selen, B. Resul, J. Stemschantz, and U. Hacksell, "Derivatives of 17-Phenyl-18,19,20-trinorprostaglandin $F_2\alpha$ Isopropyl Ester: Potential Antiglaucoma Agents", Journal of Medicinal Chemistry, Vol. 38 No. 2 (1995), pp. 289-304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_2$ has also been shown to be a stimulator of bone resorption but not as potent as $PGE_2$. Also, it has been demonstrated the $PGF_2$ has little effect on bone formation as compared to $PGE_2$. It has been suggested that some of the effects of $PGF_2$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

Formula A

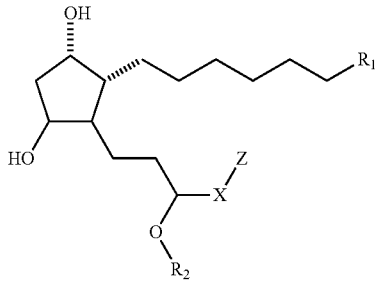

wherein $R_1$, $R_2$, X, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower alkyl" is an alkyl chain comprised of 1 to 6, preferably 1 to 3 carbon atoms.

"Aromatic ring" is an aromatic hydrocarbon ring. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring system. Bicyclic aromatic rings include ring systems wherein one ring in the system is aromatic. Preferred bicyclic aromatic rings are ring systems wherein both rings in the system are aromatic. Aromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred aromatic rings include naphthyl and phenyl. The most preferred aromatic ring is phenyl.

"Carbocyclic aliphatic ring" is a saturated or unsaturated hydrocarbon ring. Carbocyclic aliphatic rings are not aromatic. Carbocyclic aliphatic rings are monocyclic. Carbocyclic aliphatic rings contain from about 4 to about 10 carbon atoms, preferably from 4 to 7 carbon atoms, and most preferably from 5 to 6 carbon atoms in the ring. Carbocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$-$C_{12}$; more preferred are $C_1$-$C_6$; more preferred still are $C_1$-$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower heteroalkyl" is a heteroalkyl chain comprised of 1 to 6, preferably 1 to 3 member atoms.

"Heteroaromatic ring" is an aromatic ring containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings include ring systems wherein only one ring in the system is aromatic. Preferred bicyclic heteroaromatic rings are ring systems wherein both rings in the system are aromatic. Bicyclic heteroaromatic rings contain from 8 to 12 member atoms, preferably 9 or 10 in the ring. Heteroaromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo, haloalkyl, and phenyl. Preferred monocyclic heteroaromatic rings include thienyl, thiazolo, purinyl, pyrimidyl, pyridyl, and furanyl. More preferred monocyclic heteroaromatic rings include thienyl, furanyl, and pyridyl. The most preferred monocyclic heteroaromatic ring is thienyl. Preferred bicyclic heteroaromatic rings include benzo[β]thiazolyl, benzo[β]thiophenyl, quinolinyl, quinoxalinyl, benzo[β]furanyl, benzimidizolyl, benzoxazolyl, indolyl, and anthranilyl. More preferred bicyclic heteroaromatic rings include benzo [β]thiazolyl, benzo [β]thiophenyl, and benzoxazolyl.

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic. Heterocyclic aliphatic rings contain from about 4 to about 10 member atoms (carbon and heteroatoms), preferably from 4 to 7 member atoms, and most preferably from 5 to 6 member atoms in the ring. Heterocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred heterocyclic aliphatic rings include piperzyl, morpholinyl, tetrahydrofuranyl, tetrahydropyranyl and piperdyl.

"Phenyl" is a monocyclic aromatic ring which may or may not be substituted with from about 1 to about 4 substituents. The substituents may be fused but not bridged and may be substituted at the ortho, meta or para position on the phenyl ring, or any combination thereof. The substituents may be halo, acyl, cyano, alkyl, heteroalkyl, haloalkyl, phenyl, phenoxy or any combination thereof. Preferred substituents on the phenyl ring include halo and haloalkyl. The most preferred substituent is halo. The preferred substitution pattern on the phenyl ring is ortho or meta. The most preferred substitution pattern on the phenyl ring is meta.

Compounds

The subject invention involves compounds having the following structure:

Formula A

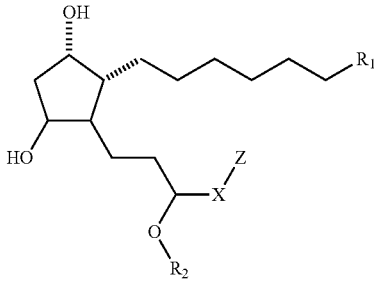

In the above structure, $R_1$ is $CO_2H$, C(O)NHOH, $CO_2R_3$, $CH_2OH$, $S(O)_2R_3$, $C(O)NHR_3$, $C(O)NHS(O)_2R_4$, or tetrazole; wherein $R_3$ is alkyl, heteroalkyl, carbocyclic aliphatic ring, heterocyclic aliphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring. Preferred $R_3$ is methyl, ethyl, and isopropyl. Preferred R, is $CO_2H$, C(O)NHOH, $CO_2R_3$, $C(O)NHS(O)_2R_4$, and tetrazole. Most preferred R, is $CO_2H$ and $CO_2R_3$.

In the above structure, $R_2$ is H or lower alkyl. The most preferred $R_2$ is H.

In the above structure, X is C═C or a covalent bond.

In the above structure, Z is an aromatic ring or a heteroaromatic ring provided that when Z is a heteroaromatic ring and X is a covalent bond, Z is attached to $C_{15}$ via a Carbon member atom. When X is C═C, preferred Z is monocyclic aromatic ring. When X is C═C, more preferred Z is furanyl, thienyl, and phenyl. When X is a covalent bond, preferred Z is a bicyclic heteroaromatic ring.

The invention also includes optical isomers, diastereomers and enantiomers of the above structure. Thus, at all stereocenters where stereochemistry is not defined ($C_{11}$, $C_{12}$, and $C_{15}$), both epimers are envisioned. Preferred stereochemistry at all such stereocenters of the compounds of the invention mimic that of naturally occurring $PGF_2$.

As can be readily seen from the description above, the invention can be placed into two subgenuses based upon the functional group "X." Formula A1 (X is C═C) and Formula A2 (X is a covalent bond) below depict these two subgenuses:

Formual A1

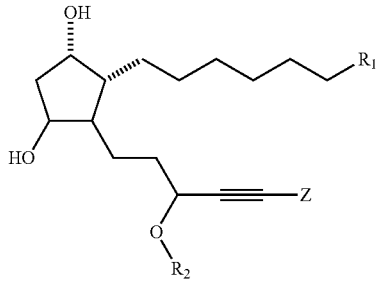

Formula A2

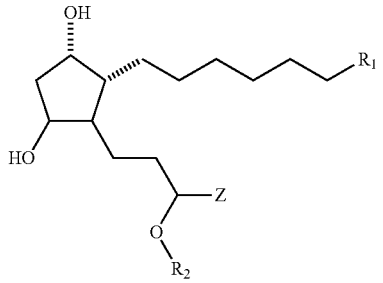

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turn-over rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. >Hacksell, "Derivatives of 17-Phenyl-18,19, 20-trinorprostaglandin $F_2\alpha$ Isopropyl Ester: Potential Antiglaucoma Agents", Journal of Medicinal Chemistry, Vol. 38 No. 2 (1995), pp. 289-304.

Compounds useful in the subject invention can be made using conventional organic syntheses. A particularly preferred synthesis is the following general reaction scheme:

Scheme 1

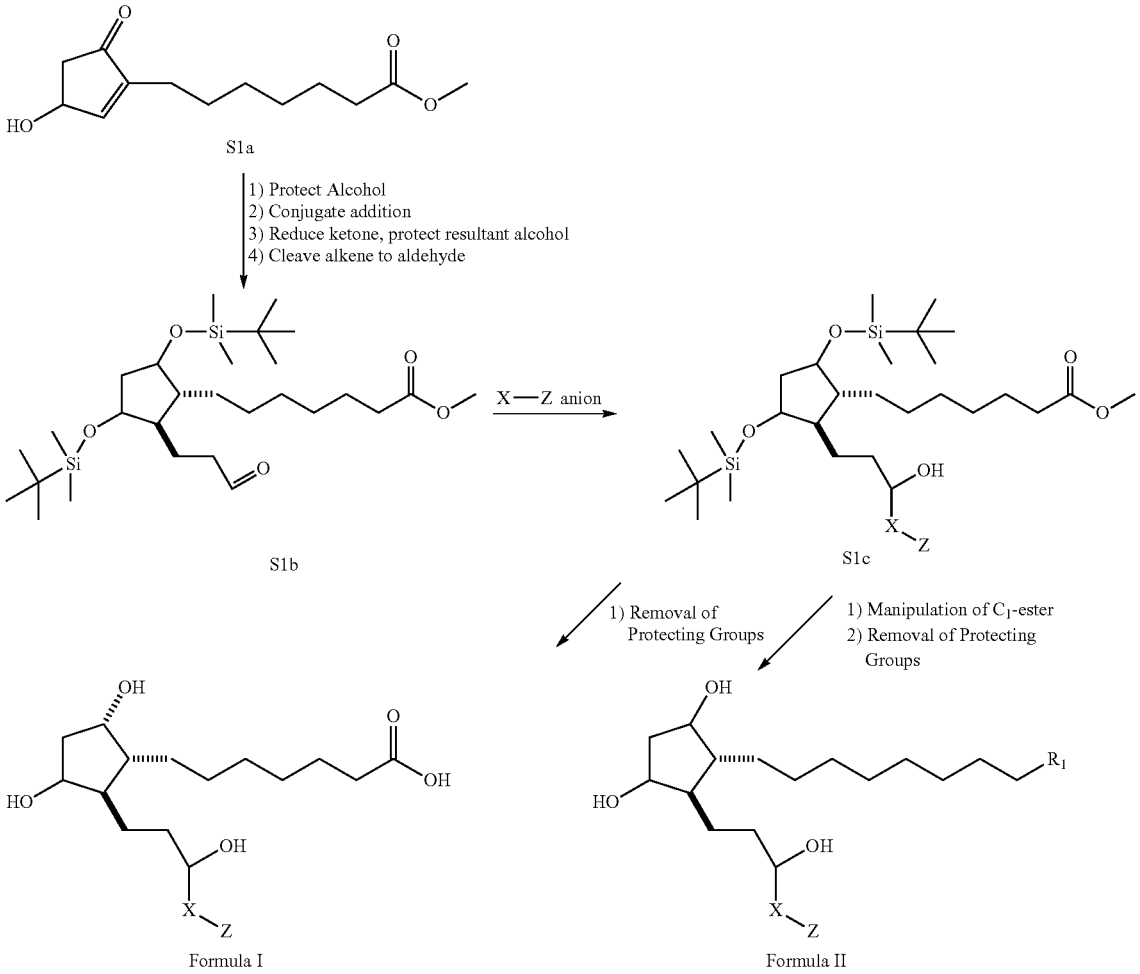

In Scheme 1, $R_1$, $R_2$, X, and Z are as defined above. The methyl 7[3-(R)-hydroxy-5-oxo-1-cyclopent-1-yl] heptanoate (S1a) depicted as starting material for Scheme 1 is commercially available (such as from Sumitomo Chemical or Cayman Chemical).

The $C_{11}$ alcohol of methyl 7-[3-(R)-hydroxy-5-oxo-1-cyclopent-1-yl] protecting group is a silyl group. In the above Scheme 1, methyl 7-[3-(R)-hydroxy-5-oxo-1-cyclopent-1-yl] heptanoate (S1a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", J. Org. Chem. Vol. 40 (1975) pp. 1460-69; and P. Knochel et. al., "Zinc and Copper Carbenoids as Efficient and Selective a'/d' Multicoupling Reagents", J. Amer. Chem. Soc. Vol. 111 (1989) p. 6474-76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuaran. The Grignard reagent is allowed to form at a temperature between 100° C. and 23° C., more preferably between 85° C. and 30° C., and most preferably between 75° C. and 65° C. The reaction time is preferably between 1 hour and 6 hours, with a more preferred reaction time being between 2 hours and 5 hours, and the most preferred reaction time being between 3 hours and 4 hours.

Once the Grignard reagent is formed, the cuprate is generated from the alkenyl magnesium species. The temperature range for cuprate formation is between −100° C. and 0° C. The preferred temperature range is between −80° C. and −20° C. The more preferred temperature range is between −75° C. and −50° C. The preferred reaction time is between 30 minutes and 6 hours. The more preferred reaction time is between 45 minutes and 3 hours. The most preferred reaction time is between 1 hours and 1.5 hours.

The alkene thus formed is isolated by methods known to one of ordinary skill in the art. Such methods include, but are not limited to, extraction, solvent evaporation, distillation, and crystallization. Preferably, the alkene is purified by flash chromatography on silica gel (Merck, 230-400 mesh) using 10% EtOAc/hexanes as the eluent. The alkene is then reacted with a hydride reducing agent and a polar, protic solvent to give the C-9 alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is between −60° C. and 0° C. The most preferred temperature range is between −45° C. and −20° C.

The resulting alcohol is isolated by methods known to one of ordinary skill in the art. Such methods include, but are not limited to, extraction, solvent evaporation, distillation, and crystallization. Preferably, the alcohol is purified by flash chromatography on silica gel (Merck, 230-400 mesh) using 20% EtOAc/hexanes as the eluent.

The resultant alcohol can be protected as described previously herein. Preferred silylating agents in this case also include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The protected or alcohol is then treated with a form of osmium, and sodium periodate in a solvent where they are both soluble. Preferred forms of osmium include osmium tetraoxide and potassium osmate. Preferred solvent systems include 1:1 mixtures of acetic acid and water and 1:1:2 mixtures of water, acetic acid and THF. The result of this treatment is the aldehyde, S1b.

The compound S1b is isolated by methods known to one of ordinary skill in the art. Such methods include, but are not limited to, extraction, solvent evaporation, distillation, and crystallization. Preferably, S1b is purified by flash chromatography on silica gel (Merck, 230-400 mesh) using 20% EtOAc/hexanes as the eluent.

The key intermediate aldehyde depicted as S1b can be reacted with a variety unsaturated carbon nucleophiles to provide the C-9 and C-11-protected 13,14-dihydro-16-tetranor prostaglandin $F_1\alpha$ derivatives depicted as S1c.

With alkyne nucleophiles, the reaction is carried out preferably at between −80° C. and 0° C., more preferably between −80° C. and −20° C., and most preferably between −80° C. and −40° C. Preferred bases for the reaction include n-butyl lithium, s-butyl lithium, t-butyl lithium, and lithium diisopropyl amide (LDA). Preferred solvents for the reaction are ether solvents. Preferred solvents include diethyl ether, and tetrahydrofuran. The most preferred solvent is tetrahydrofaran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran.

The resulting compounds depicted as S1c can then be deprotected using techniques known to one of ordinary skill in the art, and isolated yielding the 13,14-dihydro-15-substituted-15-pentanor prostaglandin Flot derivatives depicted by Formula I. Compounds depicted by Formula I are exemplified in Examples 1-43.

Compounds depicted by Formula II can be made directly from the C-9 and C-11-protected 13,14-dihydro-16-tetranor prostaglandin $F_1\alpha$ derivatives depicted as S1c by methods known to one of ordinary skill in the art. For example, the condensation of methyl esters of S1c with amines or hydroxylamine provides compounds depicted by Formula II. Compounds depicted by Formula II are exemplified in Examples 44-47. These compounds are isolated by methods known to one of ordinary skill in the art. Such methods include, but are not limited to, extraction, solvent evaporation, distillation, and crystallization.

The following non-limiting examples illustrate the compounds, compositions, and uses of the present invention.

EXAMPLES

Compounds are analyzed using $^1H$ and $^{13}C$ NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70-230 mesh; Aldrich) or (230-400 mesh; Merck) as appropriate. Thin layer chromatography analysis is performed on glass mounted silica gel plates (200-300 mesh; J. T. Baker) and visualized using uv light, 5% phosphomolybdic acid in EtOH, or ammonium molybdate/cerric sulfate in 10% aqueous $H_2SO_4$.

Example 1

Preparation of 13,14-dihydro-15-(thianaphthyl) pentanor prostaglandin $F_1\alpha$

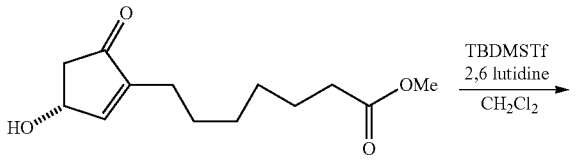

S1a

-continued

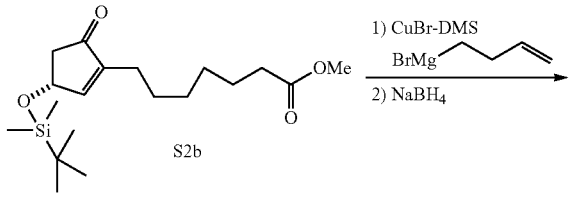

S2b

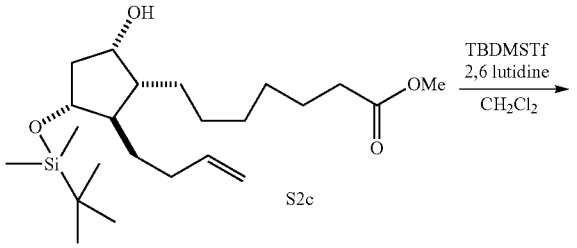

S2c

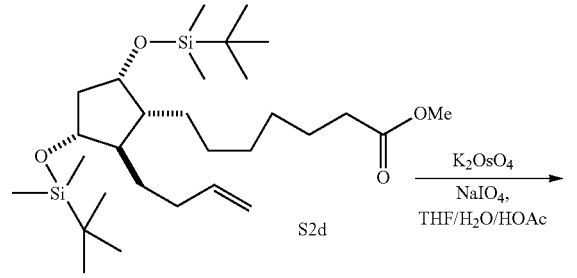

S2d

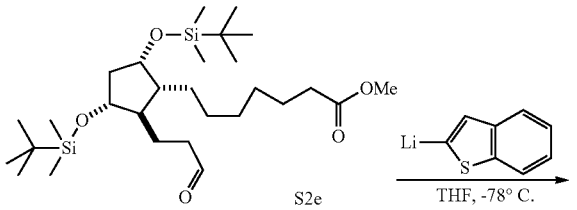

S2e

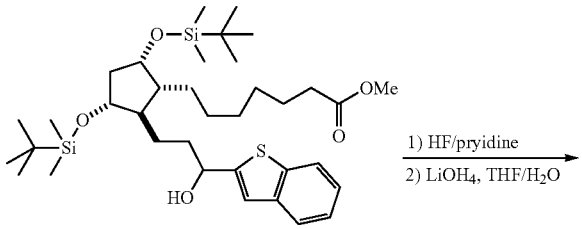

S2f

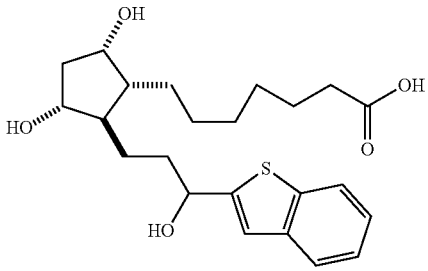

S2g a. Methyl 7-(2-oxo-4-(1,1,2,2-tetramethyl-1-silapropoxy)cyclopent-1-enyl) heptanoate S2b To a solution of Methyl-7-[3-(R)-hydroxy-5-oxo-1-cyclopenten-1-yl] heptanoate S2a (1 equiv.) in $CH_2Cl_2$ at −78° C. is added 2,6 Lutidine (1.3 equiv.) dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is distilled under vacuum (10 mm Hg) to provide the silyl ether S2b.

b. Methyl 7-(5-but-3-enyl-2-hydroxy-4-(1,1,2,2-tetramethyl-1-silapropoxy)cyclopentyl) heptanoate S2c To a slurry of $Mg^o$ powder (2 equiv.) in THF at room temperature is added one crystal of iodine (catalytic $I_2$)and 1-bromobutene (2 equiv.) dropwise over 10 minutes. The reaction proceeds to exotherm as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (20 min), the reaction is stirred for 1 hour at −78° C. The color of the reaction is dark red at this point. A solution of the ketone S2b (1 equiv.) in THF is then added dropwise over 25 minutes. The reaction is stirred at −78° C. for 15 minutes, then allowed to warm slowly to room temperature over 2 hours. The reaction is quenched with aqueous $NH_4Cl$ and the excess DMS is allowed to evaporate overnight. The reaction is partitioned between brine/$CH_2Cl_2$and the layers are separated. The aqueous layer is back-extracted with $CH_2Cl_2$ and the organic layers are combined and dried ($Na_2SO_4$). The solvent is removed in vacuo and the residue is chromatographed on $SiO_2$ (10% hexane/EtOAc) to give the ketone precursor to S2c.

The ketone precursor to S2c (1 equiv.) is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and $CH_2Cl_2$, and the layers separated. The aqueous layer is back-extracted with $CH_2Cl_2$ and the organic layers are combined and dried ($Na_2SO_4$). The solvent is removed in vacuo and the residue chromatographed on $SiO_2$ (30% EtOAc/hexanes) to give the alcohol S2c.

c. Methyl 7-(5-but-3-enyl-2,4-di(1,1,2,2-tetramethyl-1-silapropoxy) cyclopentyl) heptanoate S2d The alcohol S2c (1 equiv.) is dissolved in $CH_2Cl_2$ and cooled to 0° C. and added is 2,6 lutidine (1.3 equiv.) dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is chromatographed (10% EtOAc in hexanes) to provide the silyl ether S2d.

d. Methyl 7-(5-(3-oxopropanyl)-2,4-di(1,1,2,2-tetramethyl-1-silapropoxy) cyclopentyl) heptanoate S2e In a 50 mL round-bottomed flask, Sodium periodate (2 equiv.) and 10 mL of water are added. This is stirred until the periodate has completely dissolved. Then an equal portion of glacial acetic acid is added, followed by two portions of tetrahydrofuran. Finally, a few mole percent of potassium osmate are added, followed by the alkene S2d (1 equiv.). The reaction is stirred at room temperature under nitrogen with TLC being used to monitor the reaction. When no starting material is evident by TLC, The reaction is quenched with brine and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S2e is obtained.

e. Methyl 7-(5-(3-hydroxy-3-thianaphthylpropanyl)-2,4-di(1,1,2,2-tetramethyl-1-silapropoxy) cyclopentyl) heptanoate S2f The aldehyde S2e is dissolved in a few mL of dry THF and is added dropwise to a −78° C. THF solution of the lithium anion of thianapthylene (prepared by combining n-butyl lithium and thianaphthylene at −78° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S2f is obtained.

f. 13,14-dihydro-15-(thianaphthyl)-15-pentanor prostaglandin $F_{1\alpha}$ (S2g)

To a small round-bottomed flask, is added methyl ester S2f and 3 mL of $CH_3CN$ and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three time with 1N HCl, brine, and dried ($Na_2SO_4$). After column chromatography, (7:3, Hexane: Ethyl Acetate) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide S2g.

Examples 2-22

Examples 2-22 are prepared using substantially the same procedures as those described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 2

13,14-dihydro-15-(2-benzathiozoly)-15-pentanor Prostaglandin $F_1\alpha$

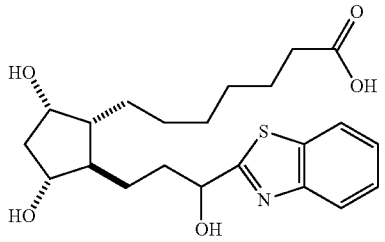

Example 3

13,14-dihydro-15-(7-fluorobenzathiozoly)-15-pentanor Prostaglandin $F_1\alpha$

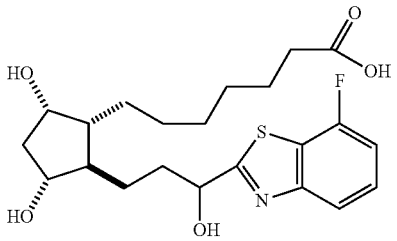

Example 4

13,14-dihydro-16-ynyl-17-(2,5-difluorophenyl)-17-trinor Prostaglandin $F_1\alpha$

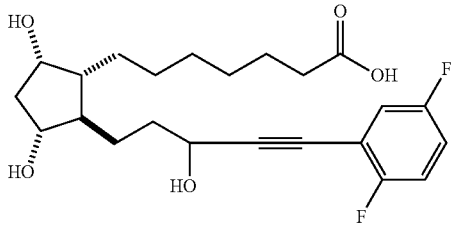

Example 5

13,14-dihydro-16-ynyl-17-(2,3-difluorophenyl)-17-trinor Prostaglandin $F_1\alpha$

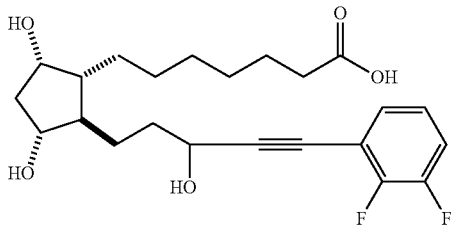

Example 6

13,14-dihydro-16-ynyl-17-(3,5-difluorophenyl)-17-trinor Prostaglandin $F_1\alpha$

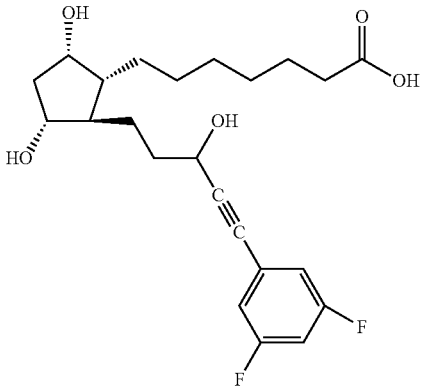

Example 7

13,14-dihydro-16-ynyl-17-(3,4-difluorophenyl)-17-trinor Prostaglandin $F_1\alpha$

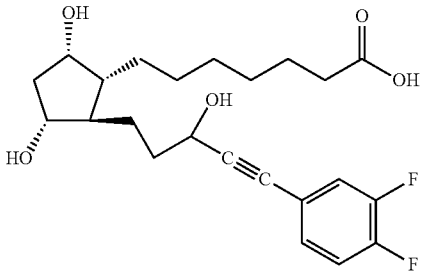

Example 8

13,14-dihydro-15-(6-fluorothianapthyl)-15-pentanor Prostaglandin $F_1\alpha$

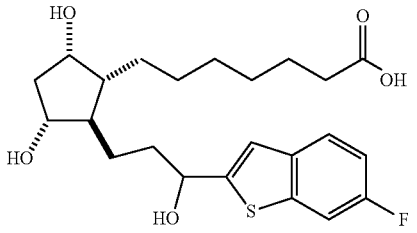

Example 9

13,14-dihydro-15-(6-ynyl-17-(2,4-difluorophenyl) 17trinor Prostaglandin $F_1\alpha$

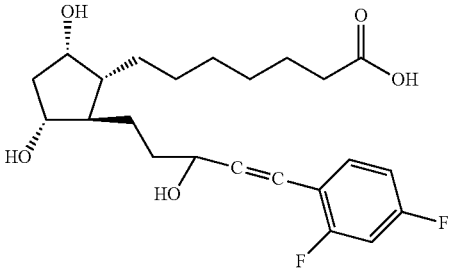

Example 10

13,14-dihydro-16-ynyl-17-(3-fluorophenyl)-17-trinor Prostaglandin F1αmethyl ester

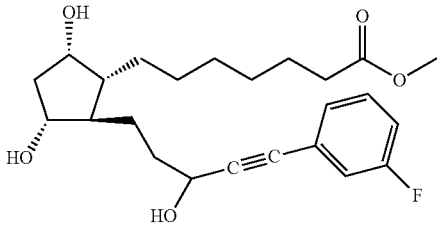

Example 11

13,14-dihydro-16-ynyl-17-(2-fluoro-4-methylphenyl)-17-trinor Prostaglandin F1α

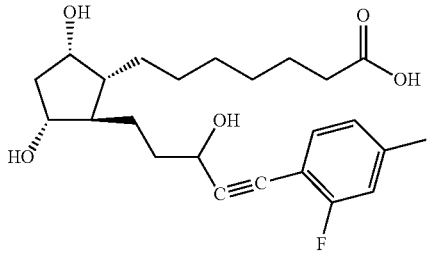

Example 12

13,14-dihydro-16-ynyl-17-(4-chlorophenyl)-17-trinor Prostaglandin F1α

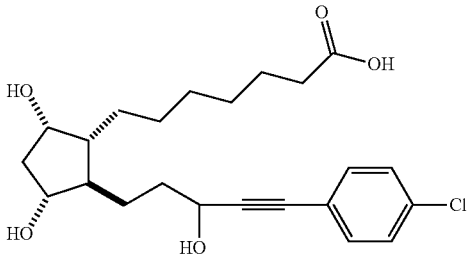

Example 13

13,14-dihydro-16-ynyl-17-phenyl-17-trinor Prostaglandin F1α isopropyl ester

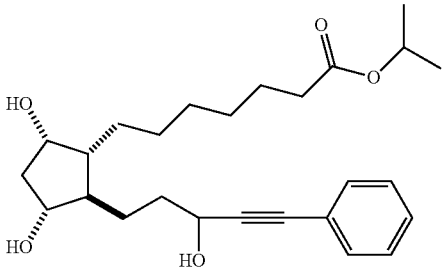

Example 14

13,14-dihydro-16-ynyl-17-(4-fluorophenyl)-17-trinor Prostaglandin F1α ethyl ester

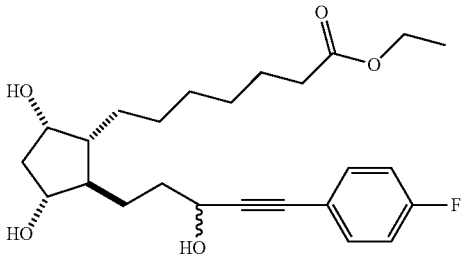

Example 15

13,14-dihydro-15-(5-fluorobenzothiazolyl)-15-pentanor Prostaglandin $F_1\alpha$ isopropyl ester

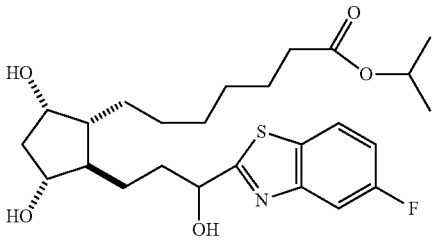

Example 16

13,14-dihydro-16-ynyl-17-(2-chlorophenyl)-17-trinor Prostaglandin F1α

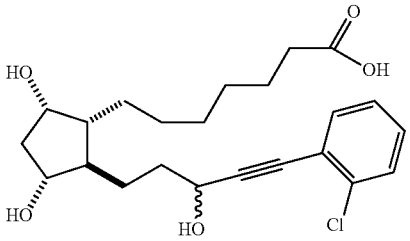

Example 17

13,14-dihydro-16-ynyl-17-(2-fluorophenyl)-17-trinor Prostaglandin F1α methyl ester

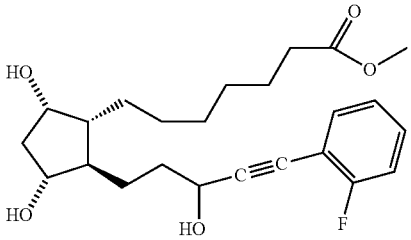

Example 18

13,14-dihydro-16-ynyl-17-(2-fluorophenyl)-17-trinor Prostaglandin F1α

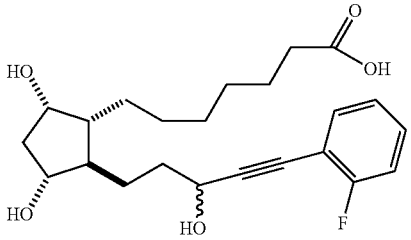

Example 19

13,14-dihydro-16-ynyl-17-(4-phenylphenyl)-17-trinor Prostaglandin F1α

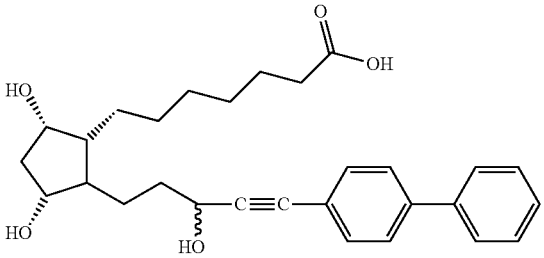

Example 20

13,14-dihydro-16-ynyl-18-phenyl-18-dinor Prostaglandin F1α

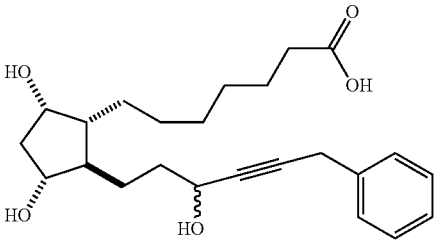

Example 21

13,14-dihydro-16-ynyl-17-(4-methylphenyl)-17-trinor Prostaglandin F1α

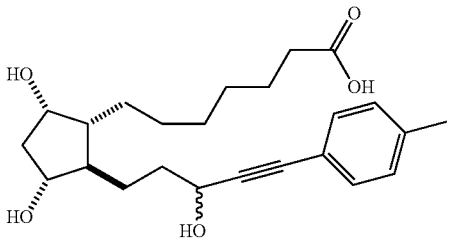

Example 22

13,14-dihydro-16-ynyl-18-(2-fluorophenyl)-18-dinor Prostaglandin F1α

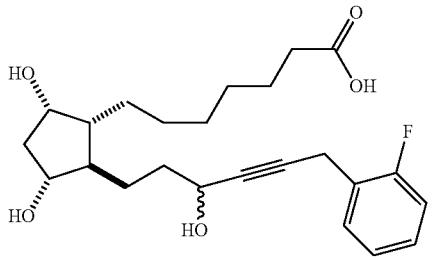

Example 23

Preparation of 13,14-dihydro-15-phenyl-15-pentanor prostaglandin F1α

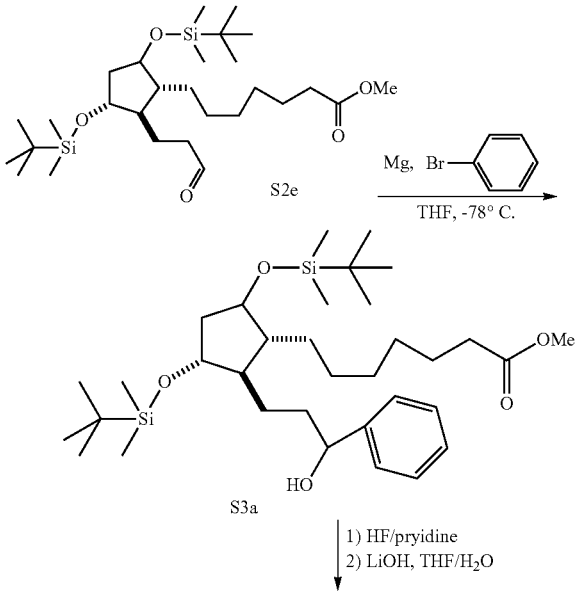

-continued

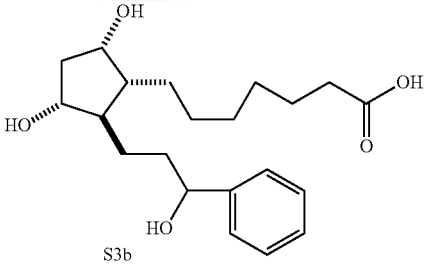

a. Methyl 7-(5-(3-hydroxy,3-phenyl-propanyl)-2,4-di (1,1,2,2-tetramethyl-1-silapropoxy) cyclopentyl) heptanoate S3a The aldehyde S2e from Example 1 is dissolved in a few mL of dry THF and is added dropwise to a −78° C. THF solution of the Grignard species (prepared by combining Magnesium and bromobenzene at 0° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S3a is obtained.

b. 13,14-dihydro-15-phenyl-15-pentanor prostaglandin F. (S3b)

To a small round-bottomed flask, is added methyl ester S3a and 3 mL of $CH_3CN$ and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three time with 1N HCl, brine, and dried ($Na_2SO_4$). After column chromatography, (97:3, dichloromethane:methanol) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide S3b.

Examples 24-35

Examples 24-35 are prepared using substantially the same procedures as those described in Example 23, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 24

13,14-dihydro-15-(4-methylphenyl)-15-pentanor Prostaglandin $F_1\alpha$

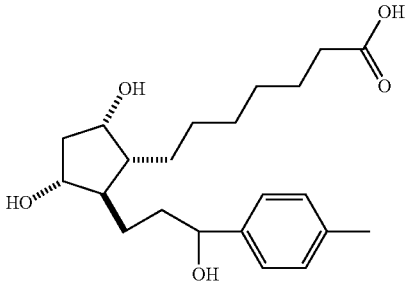

Example 25

13,14-dihydro-15-(4-trifluoromethylphenyl)-15-pentanor Prostaglandin $F_1\alpha$

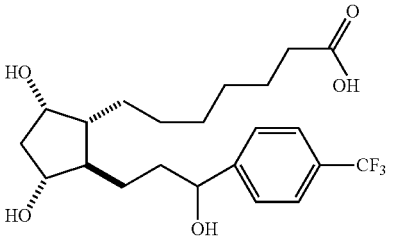

Example 26

13,14-dihydro-15 (3-trifluoromethylphenyl)-15-pentanor Prostaglandin $F_1\alpha$

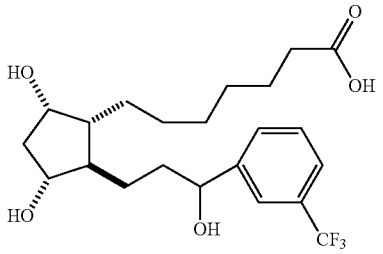

Example 27

13,14-dihydro-15-(2-fluorophenyl)-15-pentanor Prostaglandin $F_1\alpha$

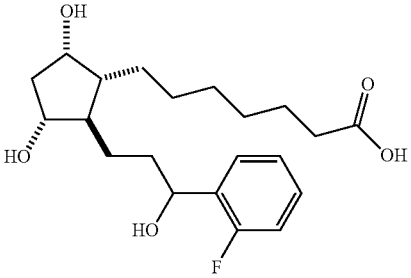

Example 28

13,14-dihydro-15-(3,5 difluorophenyl)-15-pentanor Prostaglandin $F_1\alpha$ ethyl ester

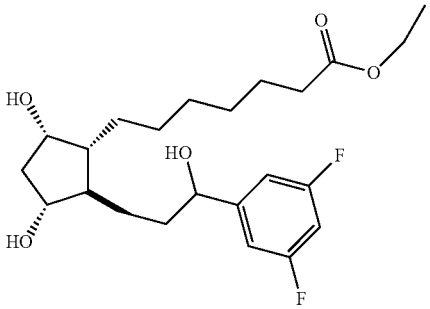

Example 29

13,14-dihydro-15-(3-chloro-4-fluoro-6-methylphenyl)-15-pentanor Prostaglandin $F_1\alpha$

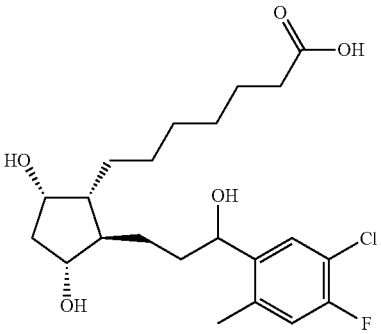

Example 30

13,14-dihydro-15 (3-pyridinyl)-15-pentanor Prostaglandin $F_1\alpha$

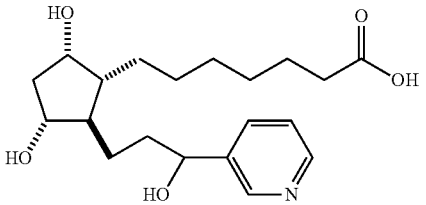

Example 31

13,14-dihydro-15 (2-chlorophenyl)-15-pentanor Prostaglandin $F_1\alpha$

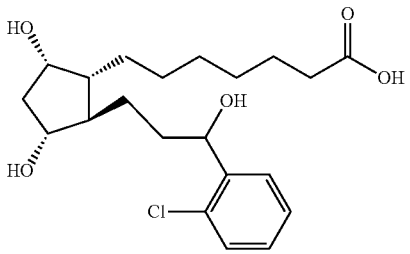

Example 32

13,14-dihydro-15 (4-phenylphenyl)-15-pentanor Prostaglandin $F_1\alpha$

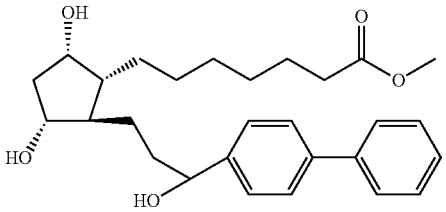

Example 33

13,14-dihydro-15-S-(2-fluorophenyl)-15-pentanor Prostaglandin $F_1\alpha$

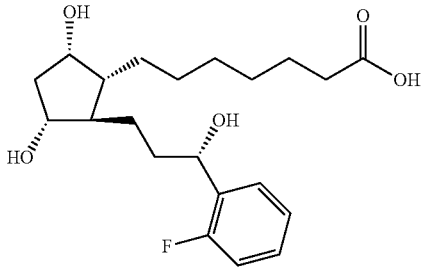

Example 34

13,14-dihydro-15-S-(2-fluoronaphthyl)-15-pentanor Prostaglandin $F_1\alpha$

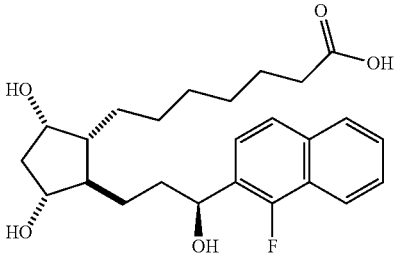

Example 35

13,14-dihydro-15 (2-fluoro-4-pyridyl)-15-pentanor Prostaglandin $F_1\alpha$ isopropyl ester

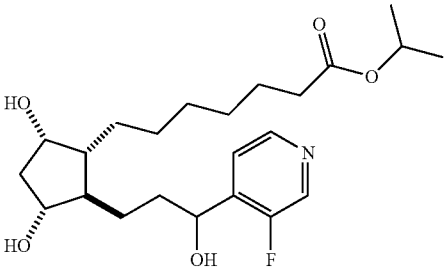

Example 36

Preparation of 13,14-dihydro-15-(6-methylnaphth-2-yl)-15-pentanor prostaglandin $F_1\alpha$:

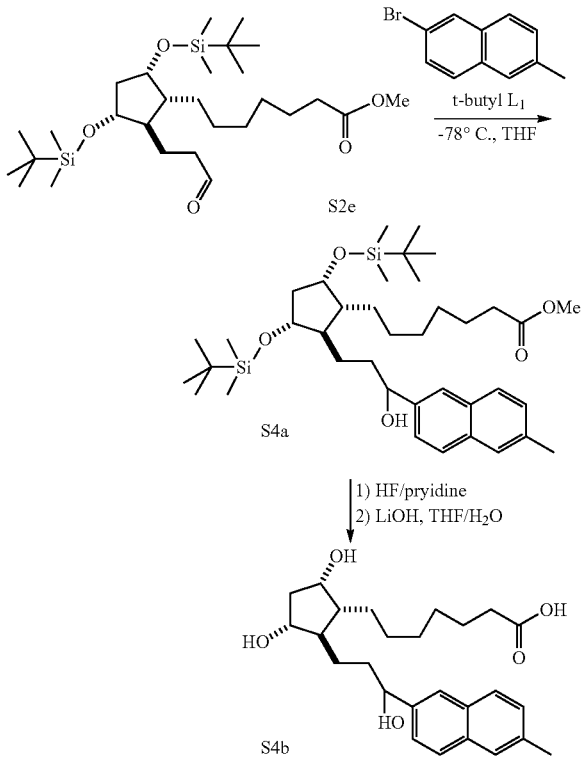

a. Methyl 7-(5-(3-hydroxy,(4-methyl-2-napththyl) propanyl)-2,4-di(1,1,2,2-tetramethyl-1-silapropoxy) cyclopentyl) heptanoate S4a The aldehyde S2e from Example 1 is dissolved in a few mL of dry THF and is added dropwise to a −78° C. THF solution of naphthyl anion (prepared by t-butyl Lithium and the naphthyl bromide at −78° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S4a is obtained.

b. 13,14-dihydro-16,17-dehydro-15-(6-methyl-2-naphthyl)-15-pentanor prostaglandin $F_1$ (S4b)

To a small round-bottomed flask, is added methyl ester S4a and 3 mL of $CH_3CN$ and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three time with 1N HCl, brine, and dried ($Na_2SO_4$). After column chromatography, (97:3, dichlormethane:methanol) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide S4b.

Examples 37-42

Examples 37-42 are prepared using substantially the same procedures as those described in Example 36, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 37

13,14-dihydro-15-(benzo[b]thiophen-5-yl)-15-pentanor prostaglandin $F_1$

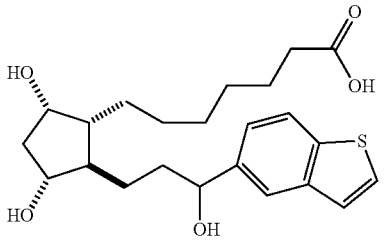

Example 38

13,14-dihydro-15-(6-benzothiazol-5-yl)-15-pentanor prostaglandin $F_1$

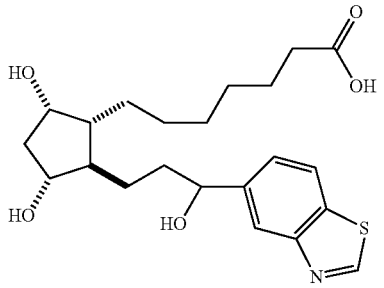

Example 39

13,14-dihydro-15-(benzo[b]furan-5-yl)-15-pentanor prostaglandin $F_1$ methyl ester

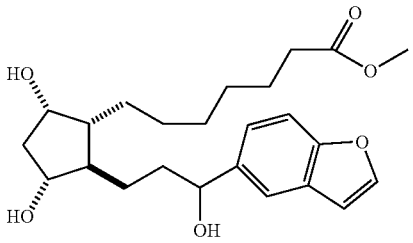

Example 40

13,14-dihydro-15-(5-fluoronaphthyl)-15-pentanor prostaglandin $F_1$

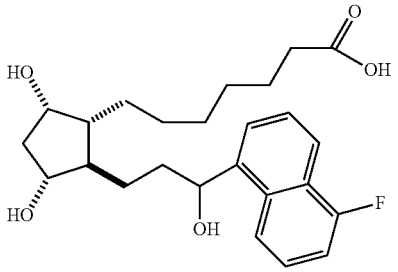

Example 41

13,14-dihydro-15-(8-fluoro-2-naphthyl)-15-pentanor prostaglandin $F_1$.

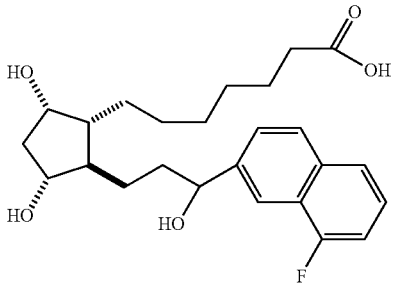

Example 42

13,14-dihydro-15-(S-trifluoromethyl-2-naphthyl)-15-pentanor prostaglandin $F_1$

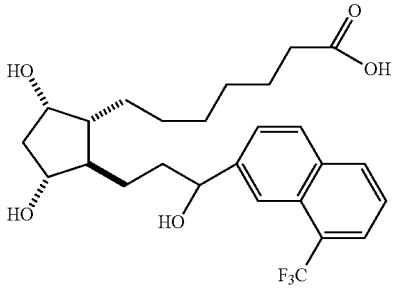

Example 43

13,14-dihydro-15-(1-fluoro-3-trifluoromethyl-2-naphthyl)-15-pentanor prostaglandin $F_1$ isopropyl ester

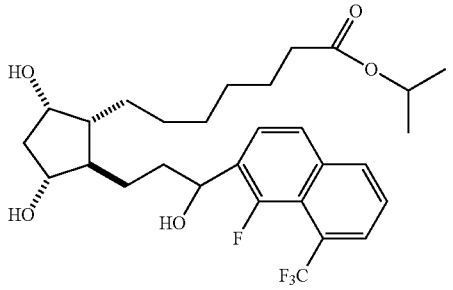

Example 44

Preparation of 13,14-dihydro-16-ynyl-17-(2-fluorophenyl)-17-trinor Prostaglandin F1α 1-hydroxamic acid:

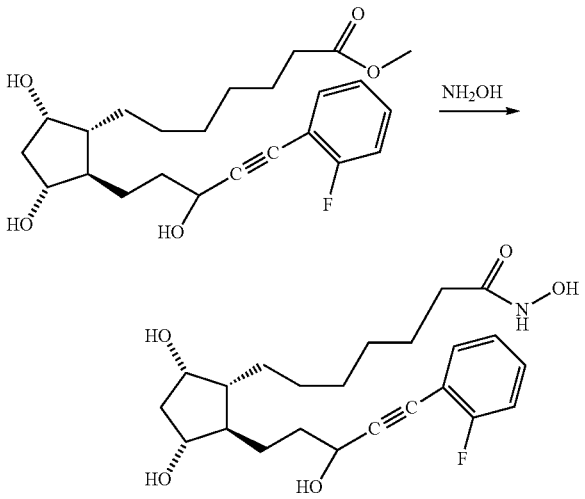

In a flame-dried 25 mL round-bottomed flask equipped with a magnetic stir bar is placed 13,14-dihydro-16,17-didehydro-17-o-fluorophenyl trinor Prostaglandin F1α methyl ester (Example 17) (1.0 equiv.) in methanol. To this solution is added hydroxylamine in methanol (1.25 equiv.). The solution stirred for a few minutes. The solution is then treated with 1N hydrochloric acid and extracted with ethyl acetate. The organic layer is washed with brine, dried over anhydrous $MgSO_4$, filtered and concentrated under reduced pressure. The residue is purified by chromatography to give 13,14-dihydro-16,17-didehydro-17-o-fluorophenyl trinor Prostaglandin F1α 1-hydroxamic acid.

Examples 45-47

Examples 45-47 are prepared using substantially the same procedures as those described in Example 44, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 45

13,14-dihydro-15-(benzathiozolyl)-15-pentanor Prostaglandin $F_1\alpha$ 1-hydroxamic acid

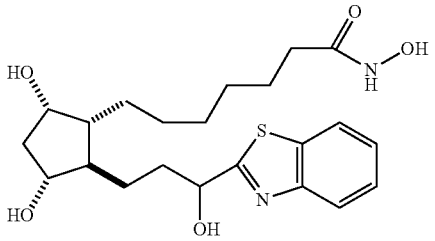

Example 46

13,14-dihydro-15-(5-fluorothianaphthyl)-15-pentanor Prostaglandin $F_1\alpha$ 1-hydroxamic acid

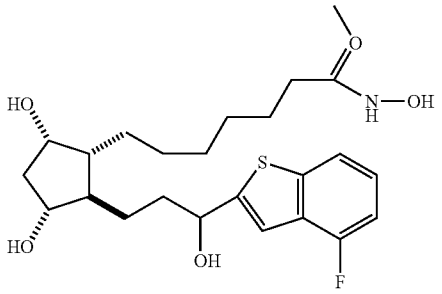

Example 47

13,14-dihydro-15-thianaphthyl-15-pentanor Prostaglandin $F_1\alpha$ 1-N-methanesulfonamide

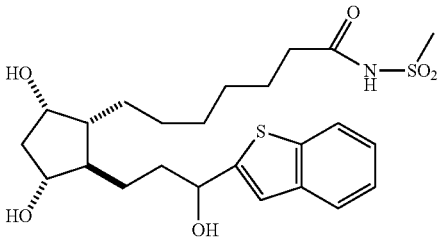

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, [and] osteoporosis*, post-menopausal osteoporosis, osteopenia, and bone fracture*.

The compounds of the present invention are useful in increasing bone volume and trabecular number through formation of new trabeculae, bone mass while maintaining a normalized bone turnover rate, and formation at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 μg/kg body weight, preferably from about 0.1 to about 100 μg/kg per body weight, most preferably form about 1 to about 50 μg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
|---|---|
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
|---|---|
| Compound of Example 32 | 1 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
|---|---|
| Compound of Example 1 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2-7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

[1. A compound having the structure:

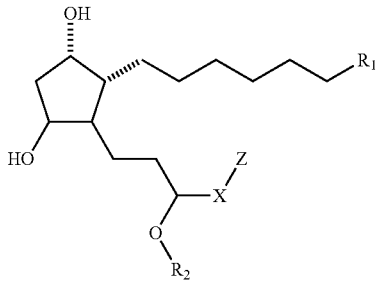

wherein a) $R_1$ is selected from the group consisting of $CO_2H$, C(O)NHOH, $C_2R_3$,$CH_2OH$, $S(O)_2R_3$, $C(O)NHR_3$. $C(O)NHS(O)_2R_4$, and tetrazole, wherein $R_3$ is alkyl, heteroalkyl, carbocyclic aliphatic ring, heterocyclic alphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring;

(b) $R_2$ is H or lower alkyl;

(c) X is a covalent bond;

(d) Z is an aromatic ring or a heteroaromatic ring provided that when Z is a heteroaromatic ring and X is a covalent bond, Z is attached to $C_{15}$ via a Carbon member atom; and (e) any optical isomer, diastereomer enantiomer of the above structure or a pharmaceutically-acceptable salt, or bio-hydrolyzable amide, ester, or imide thereof.]

2. The compound of claim [1] *4* wherein [$R_1$ is selected from the group consisting of $CO_2H$, C(O)NHOH, $CO_2R_3$, C(O))NHS$(O)_2R_4$, or tetrazole] *$R_3$ is heteroalkyl, heterocyclic aliphatic ring, monocyclic aromatic ring, or monocyclic heteroaromatic ring*.

[3. The compound of claim 2 wherein Z is a bicyclic heteroaromatic ring.]

4. [The] *A* compound [of claim 3 wherein] *having the structure:*

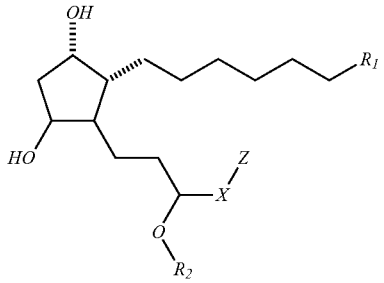

*wherein*

*(a) $R_1$ is selected from the group consisting of $CO_2H$, $CO_2R_3$, $S(O)_2R_3$, and $C(O)NHR_3$, wherein $R_3$ is alkyl, heteroalkyl, carbocyclic aliphatic ring, heterocyclic aliphatic ring, monocyclic aromatic ring, or monocyclic heteroaromatic ring;*

*(b) $R_2$ is H;*

*(c) X is a covalent bond;*

*(d)* Z is selected from the group consisting of[:] benzo[[β]](β)thiazolyl, benzo[[β]](β)thiophenyl, *thianaphthyl,* and benzoxazolyl*; and*

*(e) any optical isomer, diastereomer, enantiomer of the above structure or a pharmaceutically-acceptable salt, or bio-hydrolyzable amide, ester, or imide thereof.*

5. The compound of claim 4 wherein Z is substituted with [one] *a* substituent, said [one] substitutent being selected from the group consisting of[:] lower alkyl, halo, and haloalkyl.

[6. The compound of claim 4 wherein $R_2$ is H.]

7. The compound of claim [6] *4* wherein $R_1$ is $CO_2H$ or $CO_2R_3$.

8. A method of treating a human or other animal subject having a bone disorder, said method comprising administering to said subject a compound according to the structure:

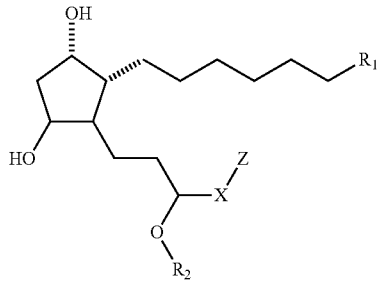

wherein (a) $R_1$ is selected from the group consisting of $CO_2H$, [C(O)NHOH,] $CO_2R_3$, [$CH_2OH$,] $S(O)_2R_3$, *and* $C(O)NHR_3$, [$C(O)NHS(O)_3R_4$, and tetrazole];

wherein [$R_1$] *$R_3$* is alkyl, heteroalkyl, carbocyclic aliphatic ring, heterocyclic aliphatic ring, monocyclic aromatic ring, or monocyclic heteroaromatic ring; [and $R_4$ is alkyl, heteroalkyl, carbocyclic aliphatic ring, heterocyclic aliphatic ring, monocyclic aromatic ring, or monocyclic heteroaromatic ring;]

(b) [$R_3$] *$R_2$* is H [or lower alkyl];

(c) X is a covalent bond;

(d) Z is [an aromatic ring or a heteroaromatic ring provided that when Z is a heteroaromatic ring and X is a covalent bond, Z is attached to $C_{15}$ via a Carbon member atom] *selected from the group consisting of benzo* (β)*thiazolyl, benzo*(β)*thiophenyl, thianaphthyl, and benzoxazolyl*; and (e) any optical isomer, diastereomer, enantiomer of the above structure or a pharmaceutically-acceptable salt, or bio-hydrolyzable[,] amide, ester, or imide thereof.

9. The method of claim 8 wherein said bone disorder is osteoporosis.

10. The method of claim 9 wherein [in] osteoporosis is post-menopausal.

11. The method of claim 9 wherein [in] osteoporosis is cortico-steroid induced.

12. The method of claim 8 wherein said bone disorder is osteopenia.

13. The method of claim 8 wherein said bone disorder is a bone fracture.

14. The method of claim 8 wherein said compound is administered orally.

15. The method of claim 8 wherein said compound is administered transdermally.

16. The method of claim 8 wherein said compound is administered intranasally.

17. A method of treating glaucoma, said method comprising administering to human or other animal a safe and effective amount of a compound according to the structure:

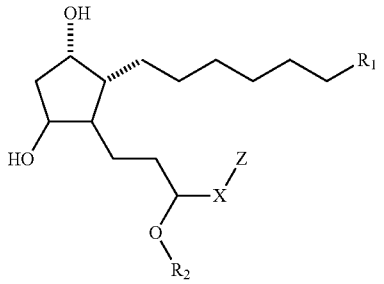

wherein (a) $R_1$ is selected from the group consisting of [$CO_3H$] *$CO_2H$*, [C(O)NHOH,] $CO_2R_3$, [$CH_2OH$,] $S(O)_2R_3$, *and* $C(O)NHR_3$, [$C(O)NHS(O)_2R_4$, and tetrazole;]

wherein [$R_1$] *$R_3$* is alkyl, heteroalkyl, carbocyclic aliphatic ring, heterocyclic aliphatic ring, monocyclic aromatic ring, or monocyclic heteroaromatic ring; [and $R_4$ is alkyl, heteroalkyl, carbocyclic aliphatic ring, heterocyclic aliphatic ring, monocyclic aromatic ring, or monocyclic heteroaromatic ring;]

(b) $R_2$ is H [or lower alkyl];

(c) X is a covalent bond;

(d) Z is [an aromatic ring or a heteroaromatic ring provided that when Z is a heteroaromatic ring and X is a covalent bond, Z is attached to $C_{15}$ via a Carbon member atom] *selected from the group consisting of benzo* (β)*thiazolyl, benzo*(β)*thiophenyl, thianaphthyl, and benzoxazolyl*; and (e) any optical isomer, diastereomer, enantiomer of the above structure or a pharmaceutically-acceptable salt, or bio-hydrolyzable[,] amide, ester, or imide thereof.

18. The method of claim 17, wherein said compound is administered [topiclally] *topically*.

*19. The compound of claim 4, wherein Z is benzo*(β) *thiophenyl.*

*20. The compound of claim 4, wherein $R_3$ is methyl, ethyl, propyl, isopropyl, n-butyl, t-butyl, or phenyl.*

*21. The compound of claim 4, wherein $R_1$ is $CO_2R_3$ and wherein $R_3$ is a substituted alkyl.*

*22. The compound of claim 4, wherein Z is thianaphthyl, $R_1$ is $CO_2R_3$, and $R_3$ is an alkyl substituted with from 1 to 4 OH groups.*

*23. A pharmaceutical composition comprising a compound having the structure:*

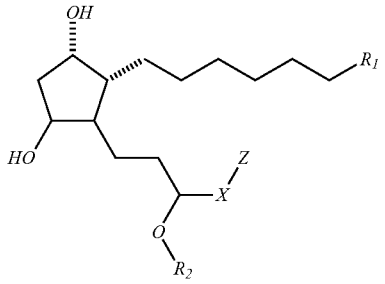

*wherein*

*(a) $R_1$ is selected from the group consisting of $CO_2H$, $CO_2R_3$, $S(O)_2R_3$, and $C(O)NHR_3$, wherein $R_3$ is alkyl, heteroalkyl, carbocyclic aliphatic ring, heterocyclic aliphatic ring, monocyclic aromatic ring, or monocyclic heteroaromatic ring;*

*(b) $R_2$ is H;*

*(c) X is a covalent bond;*

*(d) Z is selected from the group consisting of benzo*(β) *thiazolyl, benzo*(β)*thiophenyl, thianaphthyl, and benzoxazolyl; and*

*(e) any optical isomer, diastereomer, enantiomer of the above structure or a pharmaceutically-acceptable salt, or bio-hydrolyzable amide, ester, or imide thereof; and*

*(f) said composition comprising a pharmaceutically acceptable carrier.*

*24. A compound having the structure:*

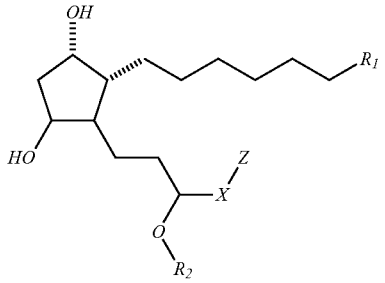

*wherein*

*(a) $R_1$ is selected from the group consisting of C(O)NHOH, $CO_2R_3$, $S(O)_2R_3$, $C(O)NHR_3$, $C(O)NHS(O)_2R_4$, and tetrazole, wherein $R_3$ is substituted alkyl, heteroalkyl, substituted carbocyclic aliphatic ring, heterocyclic aliphatic ring, monocyclic aromatic ring, or monocyclic heteroaromatic ring; and*

*$R_4$ is alkyl, heteroalkyl, carbocyclic aliphatic ring, heterocyclic aliphatic ring, monocyclic aromatic ring, or monocyclic heteroaromatic ring;*

*(b) $R_2$ is H or lower alkyl;*

*(c) X is a covalent bond;*

*(d) Z is a bicyclic heteroaromatic ring, where Z is attached to $C_{15}$ via a Carbon member atom, and wherein Z is selected from the group consisting of* benzo (β)thiazolyl, benzo (β)thiophenyl, thianaphthyl, and benzoxazolyl; and (e) any optical isomer, diastereomer, enantiomer of the above structure or a pharmaceutically-acceptable salt, or bio-hydrolyzable amide, ester, or imide thereof.

25. The compound of claim 24 wherein $R_3$ is heteroalkyl, heterocyclic aliphatic ring, monocyclic aromatic ring, or monocyclic heteroaromatic ring.

26. The compound of claim 24 wherein Z is substituted with a substituent, said substituent being selected from the group consisting of lower alkyl, halo, and haloalkyl.

27. The compound of claim 24 wherein $R_2$ is H.

28. The compound of claim 27 wherein $R_1$ is $CO_2R_3$.

29. The compound of claim 24, wherein $R_1$ is $CO_2R_3$, and wherein $R_3$ is a substituted alkyl.

30. The compound of claim 29, wherein $R_3$ is substituted with an OH.

31. The compound of claim 29, wherein $R_3$ is substituted with a substituent selected from the group consisting of halo, aryloxy, acyloxy, carboxy, monocyclic aromatic ring, monocyclic heteroaromatic ring, monocyclic carbocyclic aliphatic ring, monocyclic heterocyclic aliphatic ring, lower alkyl, and amino.

32. The compound of claim 29, wherein $R_3$ is substituted with from 1 to 4 substituents.

33. The compound of claim 29, wherein $R_3$ is substituted with from 1 to 4 OH groups.

34. The compound of claim 24, wherein Z is thianaphthyl, $R_1$ is $CO_2R_3$ and $R_3$ is an alkyl substituted with from 1 to 4 OH groups.

35. The compound of claim 34, wherein Z is substituted with a substituent, said substituent being selected from the group consisting of lower alkyl, halo, and haloalkyl.

36. The compound of claim 35, wherein Z is substituted with a substituent, said substituent being selected from the group consisting of lower alkyl, halo, and haloalkyl.

37. A method of treating a human or other animal subject having a bone disorder, said method comprising administering to said subject a compound according to the structure:

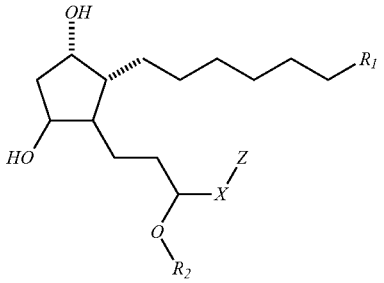

wherein (a) $R_1$ is selected from the group consisting of $CO_2H$, $C(O)NHOH$, $CO_2R_3$, $CH_2OH$, $S(O)_2R_3$, $C(O)NHR_3$, $C(O)NHS(O)_2R_4$ and tetrazole;

wherein $R_3$ is alkyl, heteroalkyl, carbocyclic aliphatic ring, heterocyclic aliphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring;

(b) $R_2$ is H or lower alkyl;

(c) X is a covalent bond;

(d) Z is an aromatic ring or a heteroaromatic ring provided that when Z is a heteroaromatic ring and X is a covalent bond, Z is attached to $C_{15}$ via a Carbon member atom; and (e) any optical isomer, diastereomer, enantiomer of the above structure or a pharmaceutically-acceptable salt, or bio-hydrolyzable amide, ester, or imide thereof.

38. The method of claim 37 wherein said bone disorder is osteoporosis.

39. The method of claim 38 wherein osteoporosis is post-menopausal.

40. The method of claim 38 wherein osteoporosis is cortico-steroid induced.

41. The method of claim 37 wherein said bone disorder is osteopenia.

42. The method of claim 37 wherein said bone disorder is a bone fracture.

43. The method of claim 37 wherein said compound is administered orally.

44. The method of claim 37 wherein said compound is administered transdermally.

45. The method of claim 37 wherein said compound is administered intranasally.

46. The method of claim 37, wherein Z is thianaphthyl, $R_1$ is $CO_2R_3$, and $R_3$ is an alkyl substituted with from 1 to 4 OH groups.

47. A method of treating glaucoma, said method comprising administering to human or other animal a safe and effective amount of a compound according to the structure:

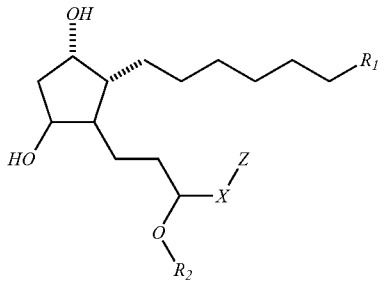

wherein (a) $R_1$ is selected from the group consisting of $C(O)NHOH$, $CO_2R_3$, $S(O)_2R_3$, $C(O)NHR_3$, $C(O)NHS(O)_2R_4$, and tetrazole, wherein $R_3$ is substituted alkyl, heteroalkyl, substituted carbocyclic aliphatic ring, heterocyclic aliphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring;

(b) $R_2$ is H or lower alkyl;

(c) X is a covalent bond;

(d) Z is a bicyclic heteroaromatic ring, provided that Z is attached to $C_{15}$ via a Carbon member atom; and (e) any optical isomer, diastereomer, enantiomer of the above structure or a pharmaceutically-acceptable salt, or bio-hydrolyzable amide, ester, or imide thereof.

48. The method of claim 47, wherein said compound is administered topically.

49. The method of claim 47, wherein $R_3$ is heteroalkyl, heterocyclic aliphatic ring, monocyclic aromatic ring, or monocyclic heteroaromatic ring.

50. The method of claim 47, wherein $R_1$ is $CO_2R_3$, and wherein $R_3$ is a substituted alkyl.

51. The method of claim 50, wherein said substituted alkyl is substituted with an OH.

52. The method of claim 47, wherein $R_3$ is an alkyl or carbocyclic aliphatic ring substituted with a substituent selected from the group consisting of hydroxyl, halo, aryloxy, acyloxy, carboxy, monocyclic aromatic ring, monocyclic heteroaromatic ring, monocyclic carbocyclic aliphatic ring, monocyclic heterocyclic aliphatic ring, lower alkyl, and amino.

53. The method of claim 52, wherein $R_3$ is substituted with from 1 to 4 substituents.

54. The method of claim 47, wherein $R_3$ is substituted with from 1 to 4 OH groups.

55. The method of claim 47, wherein Z is thianaphthyl, $R_1$ is $CO_2R_3$, and $R_3$ is an alkyl substituted with from 1 to 4 OH groups.

56. The method of claim 55, wherein Z is substituted with a substituent, said substituent being selected from the group consisting of lower alkyl, halo, and haloalkyl.

57. A pharmaceutical composition comprising a compound having the structure:

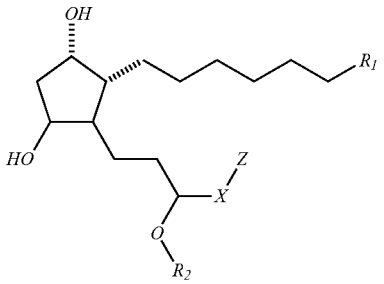

wherein (a) $R_1$ is selected from the group consisting of $C(O)NHOH$, $CO_2R_3$, $S(O)_2R_3$, $C(O)NHR_3$, $C(O)NHS(O)_2R_4$, and tetrazole, wherein $R_3$ is substituted alkyl, heteroalkyl, substituted carbocyclic aliphatic ring, heterocyclic aliphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring;

(b) $R_2$ is H or lower alkyl;

(c) X is a covalent bond;

(d) Z is a bicyclic heteroaromatic ring, provided that Z is attached to $C_{15}$ via a Carbon member atom, wherein Z is selected from the group consisting of benzo(β)thiazolyl, benzo(β)thiophenyl, thianaphthyl, and benzoxazolyl;

(e) any optical isomer, diastereomer, enantiomer of the above structure or bio-hydrolyzable amide, ester, or imide thereof; and (f) said composition comprising a pharmaceutically acceptable carrier.

58. The pharmaceutical composition of claim 57, wherein $R_3$ is heteroalkyl, heterocyclic aliphatic ring, monocyclic aromatic ring, or monocyclic heteroaromatic ring.

59. The pharmaceutical composition of claim 57, wherein Z is substituted with a substituent, said substituent being selected from the group consisting of lower alkyl, halo, and haloalkyl.

60. The pharmaceutical composition of claim 57, wherein $R_2$ is H.

61. The pharmaceutical composition of claim 57, wherein $R_3$ is substituted with a substituent selected from the group consisting of hydroxyl, halo, aryloxy, acyloxy, carboxy, monocyclic aromatic ring, monocyclic heteroaromatic ring, monocyclic carbocyclic aliphatic ring, monocyclic heterocyclic aliphatic ring, lower alkyl, and amino.

62. The pharmaceutical composition of claim 57, wherein the pharmaceutically acceptable carrier is suitable for topical application of the composition.

63. The pharmaceutical composition of claim 57, wherein Z is thianaphthyl, $R_1$ is $CO_2R_3$ and $R_3$ is an alkyl substituted with from 1 to 4 OH groups.

64. A pharmaceutical composition comprising a compound having the structure:

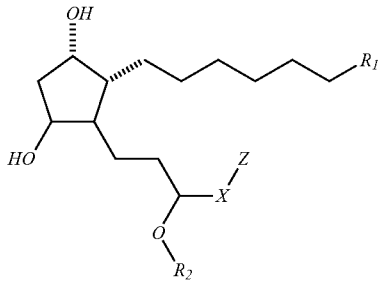

wherein (a) $R_1$ is $CO_2R_3$, wherein $R_3$ is a substituted alkyl;

(b) $R_2$ is H or lower alkyl;

(c) X is a covalent bond;

(d) Z is a bicyclic heteroaromatic ring, provided that Z is attached to $C_{15}$ via a Carbon member atom;

(e) any optical isomer, diastereomer, enantiomer of the above structure or bio-hydrolyzable amide, ester, or imide thereof; and (f) said composition comprising a pharmaceutically acceptable carrier.

65. The pharmaceutical composition of claim 64, wherein $R_3$ is substituted with an OH.

66. The pharmaceutical composition of claim 64, wherein $R_3$ is substituted with from 1 to 4 substituents.

67. The pharmaceutical composition of claim 64, wherein $R_3$ is substituted with from 1 to 4 OH groups.

68. A compound having the structure:

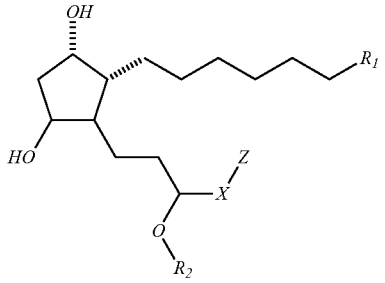

wherein (a) $R_1$ is selected from the group consisting of $C(O)NHOH$, $CO_2R_3$, $S(O)_2R_3$, $C(O)NHR_3$, and $C(O)NHS(O)_2R_4$, wherein $R_3$ is substituted alkyl, heteroalkyl, substituted carbocyclic aliphatic ring, heterocyclic aliphatic ring, monocyclic aromatic ring, or monocyclic heteroaromatic ring; and $R_4$ is heteroalkyl, carbocyclic aliphatic ring, heterocyclic aliphatic ring, or monocyclic heteroaromatic ring;

(b) $R_2$ is H or lower alkyl;

(c) X is a covalent bond;

(d) Z is a bicyclic heteroaromatic ring where Z is attached to $C_{15}$ via a Carbon member atom; and (*e*) *any optical isomer, diastereomer, enantiomer of the above structure or a pharmaceutically-acceptable salt, or bio-hydrolyzable amide, ester, or imide thereof.*

*69. A method of treating glaucoma, said method comprising administering to human or other animal a safe and effective amount of a compound according to the structure:*

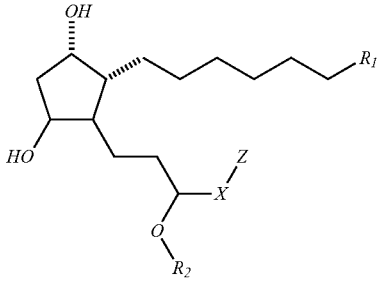

*wherein*

(*a*) $R_1$ *is selected from the group consisting of* $C(O)NHOH$, $CO_2R_3$, $S(O)_2R_3$, $C(O)NHR_3$, *and* $C(O)NHS(O)_2R_4$, *wherein* $R_3$ *is substituted alkyl, heteroalkyl, substituted carbocyclic aliphatic ring, heterocyclic aliphatic ring, monocyclic aromatic ring, or monocyclic heteroaromatic ring; and*

$R_4$ *is heteroalkyl, carbocyclic aliphatic ring, heterocyclic aliphatic ring, or monocyclic heteroaromatic ring;*

(*b*) $R_2$ *is H or lower alkyl;*

(*c*) *X is a covalent bond;*

(*d*) *Z is a bicyclic heteroaromatic ring where Z is attached to* $C_{15}$ *via a Carbon member atom; and*

(*e*) *any optical isomer, diastereomer, enantiomer of the above structure or a pharmaceutically-acceptable salt, or bio-hydrolyzable amide, ester, or imide thereof.*

* * * * *